(12) United States Patent
Alessi et al.

(10) Patent No.: US 7,587,280 B2
(45) Date of Patent: Sep. 8, 2009

(54) GENOMIC DATA MINING USING CLUSTERING LOGIC AND FILTERING CRITERIA

(75) Inventors: Enrico Alessi, Catania (IT); Salvatore Oliveri, Aci Catena (IT); Flavio Di Francesco, Gela (IT); Antonella Licciardello, Misterbianco (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 424 days.

(21) Appl. No.: 10/723,323

(22) Filed: Nov. 26, 2003

(65) Prior Publication Data

US 2004/0191804 A1     Sep. 30, 2004

(30) Foreign Application Priority Data

Dec. 23, 2002   (EP)   ................... 02425791

(51) Int. Cl.
*G01N 33/48*   (2006.01)
(52) U.S. Cl. ....................................... 702/19
(58) Field of Classification Search .................. 702/19
See application file for complete search history.

(56) References Cited

U.S. PATENT DOCUMENTS

| 2002/0156587 | A1 | 10/2002 | Woolf et al. | |
| 2003/0224344 | A1* | 12/2003 | Shamir et al. | 435/4 |
| 2004/0128080 | A1* | 7/2004 | Tolley | 702/20 |

FOREIGN PATENT DOCUMENTS

WO    WO 02/093453    11/2002

OTHER PUBLICATIONS

Dougherty et al. "Inference from Clustering with Appliation to Gene-Expression Mcroarrays." Journal of Computational Biology (Jan. 2002) vol. 9, No. 1, pp. 105-126.*

Quackenbush, John, "Computational Analysis of Microarray Data," Nature Reviews Genetics (2001) vol. 2, pp. 418-427.*

Getz, et al., "Coupled two-way clustering analysis of gene microarray data", Proceedings of the National Academy of Sciences of USA, National Academy of Science, Washington, US, vol. 97, No. 22, Oct. 24, 2000, pp. 12079-12084, XP002953907, ISSN: 0027-8424.

D'Haeseleer, et al., "Genetic network inference: from co-expression clustering to reverse engineering", Bioinformatics, Oxford University Press, Oxford, GB, vol. 16, No. 8, Aug. 2000, pp. 707-726, XO00108839, ISSN: 1367-4803.

Tavazoie, et al., "Systematic determination of genetic network architecture", Nature Genetics, Nature America, New York, US, vol. 22, Jul. 1999, pp. 281-285, XP002953903, ISSN: 1061-4036.

Tamayo, et al., "Interpreting patterns of gene expression with self-organizing maps: Methods and application to hematopoietic differentiation", Proceedings of the National Academy of Sciences of USA, National Academy of Science, Washington, US, vol. 96, Mar. 1999, pp. 2907-2912, XP000942169, ISSN: 0027-8424.

Yeung, et al., "Clustering gene-expression data with repeated measurements", Genome Biology 2003, 4:R34, http://genomebiology.com/2003/4/R34.

Woolf, et al., "A fuzzy logic approach to analyzing gene expression data", Physiol Genomics, vol. 3, pp. 9-15, 2000, http://physiolgenomics.physiology.org.

* cited by examiner

*Primary Examiner*—Jerry Lin
(74) *Attorney, Agent, or Firm*—Gardere Wynne Sewell LLP

(57) ABSTRACT

A method for automatic analysis of genomic information in order to determine relationships among genes allows one to determine complex relationships among genes. First a clustering algorithm is chosen and is applied to the table, obtaining sub-tables of data relative to groups of genes that satisfy the chosen clustering criterion. Therefore, all possible combinations of pair of sub-tables are generated and characteristic parameters are calculated for genes contained in these sub-tables. Finally, for each combination a characteristic value is calculated with a decision algorithm defined in function of these parameters, by considering the genes of the combination as constituting a "Gene Network" if this characteristic value exceeds a pre-defined threshold. The method is preferably is implemented by a relative system of identification of groups of co-expressed and co-regulated genes comprising an intelligent fuzzy sub-system trained off-line identified by a neural network.

21 Claims, 4 Drawing Sheets

NCBI Reference Sequences (RefSeq)                                              ?

Category: PROVISIONAL
mRNA:      NM_017106
Pr tein:   NP_058802  chloride channel 5              BL
Domains:   CBS domain                        score: 103
           Biotin synthase                   score: 86
           Voltage gated chloride            score: 858
           channels
           Domain in cystathionine beta-     score: 108
           synthase and other proteins.
GenBank    D50497
Source:

GenBank Sequences                                                              ?

Nucleotide   Type    Protein
D50497       m       BAA09091                         BL
Z56277       m       CAA91216                         BL

Function        Submit GeneRIF                                                 ?

Gene Ontology™:
   Term              Evidence    Source    Pub
 • membrane          IEA         RGD
 • chloride transport IEA        RGD

FIG. 3

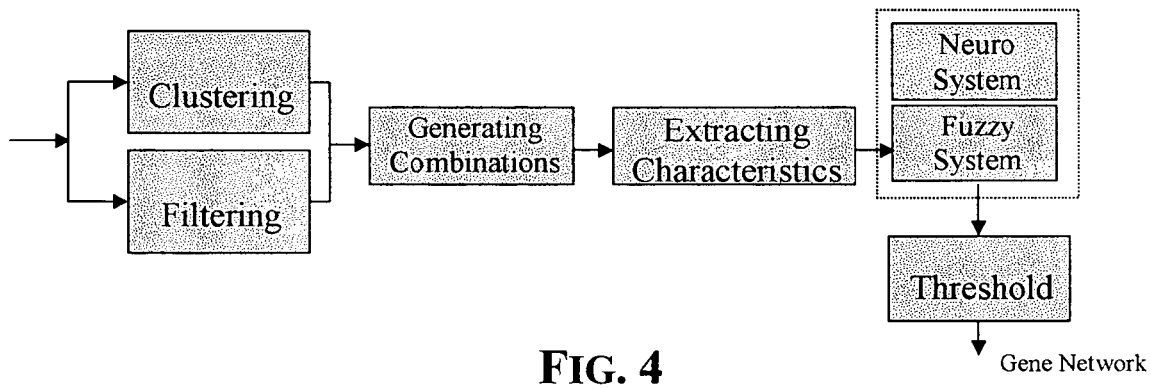

FIG. 4

| P1 | P2 | P3 | P4 | P5 | P6 | Out |
|----|----|----|----|----|----|-----|
| 0.90 | 0.90 | 1.00 | 0.83 | 1.00 | 0.90 | 1.00 |
| 0.10 | 0.10 | 1.00 | 1.00 | 0.47 | 0.28 | 0.00 |
| 0.90 | 0.90 | 1.00 | 1.00 | 1.00 | 0.53 | 0.00 |
| 0.90 | 0.60 | 1.00 | 0.69 | 1.00 | 0.75 | 1.00 |
| 0.00 | 0.00 | 0.00 | 0.92 | 0.92 | 0.05 | 0.00 |
| 0.90 | 0.00 | 1.00 | 1.00 | 1.00 | 1.00 | 1.00 |
| 0.58 | 0.44 | 1.00 | 0.67 | 0.67 | 0.60 | 1.00 |
| 0.70 | 0.43 | 1.00 | 0.42 | 1.00 | 0.67 | 0.00 |
| ... | ... | ... | ... | ... | ... | ... |
| 0.84 | 0.47 | 1.00 | 0.00 | 1.00 | 0.63 | 0.00 |
| 0.00 | 0.00 | 0.00 | 1.00 | 0.92 | 0.05 | 0.00 |

GENOMIC DATA MINING USING CLUSTERING LOGIC AND FILTERING CRITERIA

PRIOR RELATED APPLICATIONS

This application claims priority to EP 02425791.7 filed on Dec. 23, 2002, the disclosure of which is hereby incorporated by reference.

FIELD OF THE INVENTION

The present invention generally relates to genomic analysis. More particularly, it relates to a data mining system for the analysis of gene expression data that employs both clustering criteria and logic filtering criteria and allows clustering according to multiple parameters.

BACKGROUND OF THE INVENTION

In the year 2001 the first draft of the sequence of the human genome was completed. As of November 2003, over 164 complete genomes had been published, including mouse, fruit fly, pufferfish and yeast. This wealth of knowledge provides researchers with fundamental tools for preventing or treating diseases, which in many cases are considered to be caused or exacerbated by the simultaneous action of different genes.

In traditional genomic study, a single gene was studied at a time. However, genomic research is nowadays directed towards the development of technologies that allow a parallel analysis of thousands of genes at a time.

The so-called "gene-chips" or "DNA-chips" are extraordinary tools for studying patterns of gene expression. Gene-chips are large arrays of nucleic acid probes, arranged in matrix format on a surface such as a microscope slide. Gene-chips can contain hundreds to hundreds-of-thousands of such probes. Thus, the devices are called "arrays" or "microarrays," and with future advances in array printing even "nanoarrays" will become practical.

These recent advances allow researchers to measure expression levels for thousands of genes simultaneously, across different conditions and over time. Analysis of data produced by such experiments offers potential insight into gene function and regulatory mechanisms. However, a key step in the analysis is the detection of groups of genes that have similar expression patterns. The corresponding algorithmic problem is to group or "cluster" gene expression patterns and correlate these with a variety of different parameters, such as time, drug response, disease status, patient, and the like.

Modern data mining technology can handle all three primary learning tasks: classification, regression, and clustering. However, clustering is used most commonly in the data mining of genomic information and several clustering algorithms are available.

In the general parlance of bioinformatics a clustering problem consists of n elements and a characteristic vector for each element. A measure of similarity is defined between pairs of such vectors. In gene expression, elements will be genes, the vector of each gene will contain its expression levels under each of the conditions, and similarity can be measured, for example, by correlation coefficient between vectors. The goal is to partition the elements into subsets, which are called clusters, so that two criteria are satisfied: 1) Homogeneity—whereby elements inside a cluster are highly similar to each other; and 2) Separation—whereby elements from different clusters have low similarity to each other.

There is a very rich literature on cluster analysis going back over three decades. Several algorithmic techniques have been used in clustering gene expression data, including hierarchical clustering, such as Cluster Identification via Connectivity Kernals (CLICK) or the divisive hierarchical algorithm called DIANA, model based approaches such as the Beyesion Infinite Mixture Model (IMM), and mixed approaches such as a finite Gaussian mixture model-based hierarchical clustering algorithm from MCLUST. There are also iterative approaches such as k-means and Cluster Affinity Search Technique (CAST). There are other approaches such as simulated annealing, self organizing maps (SOM), and graph theoretic approaches. There are even several publicly available software packages for clustal analysis, including MCLUST, Vera and SAM, KNNimpute, dCHIP and the BioConductor project.

However, a limit of the known data mining techniques is that it is not possible to identify groups or sequences of genes by simultaneously applying a plurality of properly weighed criteria for grouping according to gene expression with time and a variety of specific properties of particular interest.

SUMMARY OF THE INVENTION

The invention generally relates to a method of analysis of genomic information in order to determine relationships among genes. The method of this invention allows one to determine complex relationships among genes that go beyond the simple clustering operations of the known methods of determining which genes are co-expressed or co-regulated.

The method of this invention is applicable to a table of data relative to the evolution of the gene expression with time or relative to different stress conditions, and does not depend on the method used for obtaining the data.

First, a certain clustering algorithm is chosen and applied to the data of the table, obtaining sub-tables of data relative to groups of genes (CLUSTERS). Therefore, all possible pairing combinations of the sub-tables of data are generated and characteristic parameters are calculated for genes contained in these sub-tables.

Then, for each combination a characteristic value is calculated with a decision algorithm defined in function of these parameters, by considering the genes of the combination as constituting a 'Gene Network' if the characteristic value exceeds a pre-defined threshold.

Preferably, a certain group of logic filtering criteria of the data of the table is chosen, generating other sets of sub-tables of data of groups of genes that satisfy the respective logic criterion. Pair combinations of the sub-tables, obtained with logic or clustering criteria, are calculated.

Preferably, the decision algorithm is a fuzzy logic algorithm, the antecedents and consequents of which are defined in function of the characteristic parameters The method of this invention may be implemented by a relative system of identification of groups of co-expressed and co-regulated genes. The core of such an identification system is an intelligent sub-system that processes the characteristic parameters of groups of genes and outputs data of groups of genes identified as 'Gene Networks.' Preferably, this intelligent sub-system is an off-line trained, fuzzy logic processor sub-system structured as a neural network.

DESCRIPTION OF THE DRAWINGS

A more complete understanding of the method and apparatus of the present invention may be acquired by reference to the following Detailed Description when taken in conjunction with the accompanying Drawings wherein:

FIG. 3 is an example of a report obtained carrying out a query at the website LocusLink. The report shows that kind of information that is already known about a particular gene and might be included in clustering techniques. In this example, known information includes that the protein is a membrane protein involved in ion transport, and a variety of known domains are found in the protein;

FIG. 4 depicts a preferred embodiment of a system of the invention;

DESCRIPTION OF THE INVENTION

The application makes reference to a number of Tables, the identification and general contents of which are as follows:

Table 1 is sample table of data relating to gene expression;

Table 2 contains a set of values of gene expression for the yeast *S. cerevisiae* in different instants;

Table 3 contains data extracted from the Saccharomyces Genome Database for several genes mentioned in Table 2;

Table 4 contains data relating to several genes from Table 2 that have been grouped in a CLUSTER;

Table 5 shows possible combinations between two groups of genes and the characteristic value associated with each combination;

Tables 6 and 7 show data relative to genes grouped in CLUSTERS 26 and 30;

Table 8 shows levels of gene expression of the combination among CLUSTERS of Tables 6 and 7;

Table 9 shows levels of expression of Table 8 normalized to range between 0 and 1; and Table 10 shows values of increments of levels of expression of Table 9.

The method of the invention allows one to identify groups of genes ('Gene Networks') that are likely to be involved in a particular cellular process. This method is based on a decision algorithm that identifies groups of co-expressed or co-regulated genes using both clustering criteria and logic filtering criteria.

Table 1 shows a sample table of data relating to gene expression.

TABLE 1

| ORF | 0 Minutes | 30 Minutes | 1 Hour | 2 Hours |
|---|---|---|---|---|
| YAL001C | 1 | 1.3 | 2.4 | 5.8 |
| YAL002W | 0.9 | 0.8 | 0.7 | 0.5 |
| YAL003W | 0.8 | 2.1 | 4.2 | 10.1 |
| YAL005C | 1.1 | 1.3 | 0.8 | |
| YAL010C | 1.2 | 1 | 1.1 | 4.5 |

From each group of genes, characteristic parameters are calculated and, with a decision algorithm based on these characteristic parameters, a characteristic value is calculated. When this characteristic value exceeds a certain pre-established threshold, the relative group of genes is identified as a constituent of a "Gene Network," otherwise it is discarded.

The remarkable advantage of the this technique is the fact that the limits of prior methods based exclusively on clustering are overcome, and the invention allows one to identify a group of genes as a "Gene Network" according to a number of differently combined criteria.

Preferably, the decision algorithm is a fuzzy logic algorithm configured such to identify correlations among genes within a large amount of data, corresponding to the time variable of gene expression or to different cellular conditions.

Figure 1:
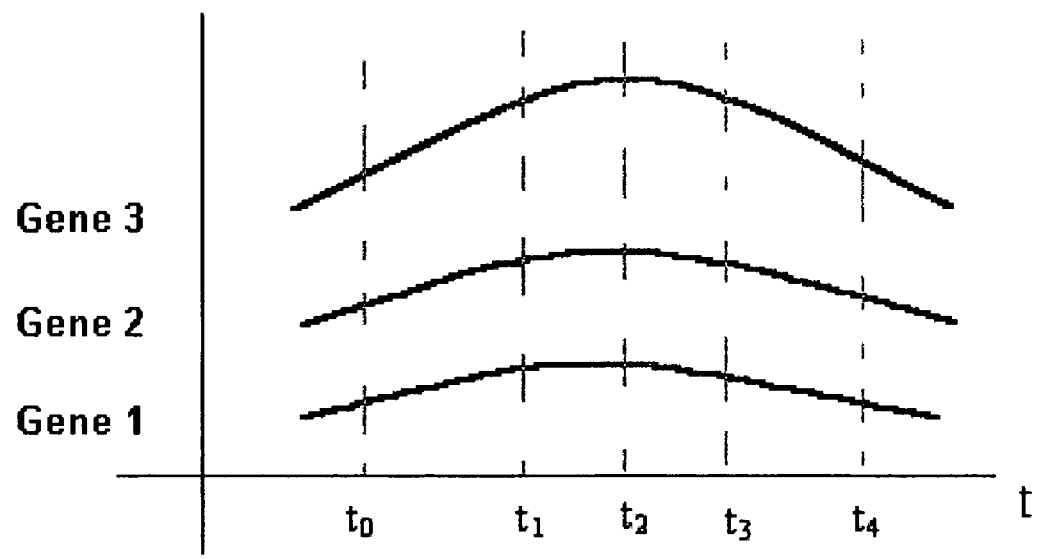
FIG. 1 is a diagram of levels of gene expression at different instants relating to the same sample of DNA.
Figure 2:
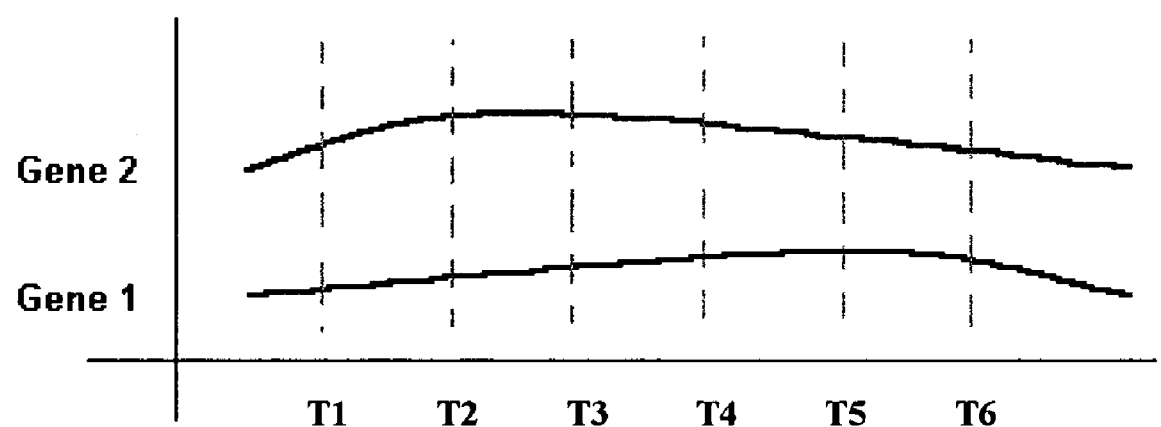
FIG. 2 is an interpolated diagram of the levels of gene expression at a certain pre-established instant, relative to different samples (T1, . . . , T6) of DNA.

Reference and brief description of FIGS. 1-3 has already been provided.

A schematic representation of a preferred embodiment of a system implementing the method of this invention is shown in FIG. 4.

The system includes three sub-systems:
1. A pre-processing sub-system (CLUSTERING, FILTERING), that generates groups of tables using clustering criteria and logic filtering criteria;
2. A processing sub-system (GENERATING COMBINATIONS, EXTRACTING CHARACTERISTICS) that generates groups of genes that are Gene Networks candidates, by combining pairs of sub-tables and extracting characteristic parameters for each combination of genes; and
3. An intelligent sub-system (NEURO SYSTEM, FUZZY SYSTEM, THRESHOLD), trained off-line, that output groups of genes identified as Gene Networks.

The intelligent sub-system is preferably a fuzzy logic system that is trained off-line. It is capable of attributing to each candidate group of genes a characteristic value using a soft computing decision making algorithm (see, e.g., reference (22)). If this characteristic value exceeds a pre-established THRESHOLD, the relative group of genes is identified as constituting a Gene Network.

Clustering and Filtering: The pre-processing sub-system generates similar groups of gene sequences using clustering criteria and logic filtering criteria. There are plenty of clustering criteria in literature, including but not limited to those cited herein:
1. Hierarchical Agglomerative;
2. Non hierarchical K-means;
3. Hierarchical sequential K-means;
4. Non hierarchical SOM; and
5. Non exclusive Fuzzy Clustering.

For each gene, m values of gene expression are reported, relating to m experiments carried out at different instants or under different conditions. The system generates a certain number of groups of genes (CLUSTERS) according to the criterion used and the initial settings chosen for the processing.

In order to study Gene Networks, it is desirable to select groups of genes that present characteristics in addition to their similarity of time expression profiles. This is made possible through filtering techniques that select groups of genes, depending on the value assumed by one or more attributes of the gene itself.

The criteria to be used must be chosen as appropriate for grouping similar gene sequences. For example, when the influence of extended groups of genes among them and towards single genes must be verified, it is preferable to use a stringent logic filtering criterion and clustering algorithms that generate extended groups of CLUSTERS. Stringent logic filtering refers to a logic filtering criterion defined by plural logic conditions to be simultaneously satisfied and by virtue of which is likely to select only a relatively small number of genes. Thus, for identifying a group of correlated genes in a very numerous group of genes, or for finding genes belonging to a numerous group of genes that are correlated to one specific gene, it is desirable to use a clustering algorithm likely to produce a numerous group of genes, in combination with a "stringent" logic filtering for identifying a relatively small group of correlated genes. Groups of genes that may be correlated are identified by performing a clustering operation in combination with a filtering operation. Such a choice may consist of a single linkage hierarchical method coupled to the metric used for updating the matrix of distances.

A filtering criterion is any logic criterion that an user may impose on the data. For example, a filtering criterion may consist of selecting all the genes whose level of expression exceeds a certain value at the beginning of the experiment. Another filtering criterion may be that of considering those genes whose expression level changes on challenge with a test drug, and the like.

Generation of combinations and composition of groups of gene candidates to be a Gene Network: Let us suppose we have generated K sub-tables of genes (CLUSTER) with a certain clustering criterion and M sub-tables of genes (FILTER) with certain logic filtering criteria. According to the method of this invention, all possible groups of genes are generated by combining in pairs the sub-tables:

1. $\binom{K}{2} = \frac{K!}{(K-2)! * 2!} = \frac{K*(K-1)}{2}$

CLUSTER-CLUSTER combinations;

2. $\binom{M}{2} = \frac{M!}{(M-2)! * 2!} = \frac{M*(M-1)}{2}$

FILTER-FILTER combinations; and

3. K*M CLUSTER-FILTER combinations.

Preferably, among these combinations, the ones that generate groups of genes with a number of genes smaller than a certain pre-established threshold are discarded together with the combinations that generate groups of genes already obtained in a previous combination.

Each gene of the combination may be labeled with a string that indicates the group it belongs to. For example, a gene is labeled C2 if the group it belongs to is the cluster 2. In a combination FILTER-FILTER or CLUSTER-FILTER, a gene present in both groups is labeled $F_iF_j$ or $C_iF_j$, where the subscripts i and j are the indexes of the CLUSTER or the FILTER the gene is coming from.

When the aim is to determine how the behavior of a certain gene influences a whole CLUSTER, it is preferable to generate combinations among a FILTER constituted only by that gene and groups (CLUSTERS) constituted by more genes.

Extraction of characteristics: The most significant phase is the extraction of characteristics because they indicate the type of correlations that must be identified. According to an innovative feature of the present invention, numerical parameters, tied to the gene expression profile, and parameters that, in contrast have a semantic meaning are both used. Mixed parameters that are combination of both elements may also be used.

A sample semantic parameter that is considered in Gene Network analysis is the percentage of genes of the combination with the same functional domain. A number ranging from 0 to 1 is associated to this percentage. When the value of the parameter is 1, all the genes of the considered combination have the same functional domain. When the value is null, the genes do not have any common domain, while in all other cases the value of this parameter is comprised between 0 and 1.

Similarly, another semantic parameter relates to the percentage of genes that have ontologies belonging to the same category. It is evident that other semantic parameters could be considered by extending this analysis to other semantic characteristics of gene sequences. It is emphasized that these parameters refer to semantic characteristics, but are expressed in numerical form.

According to one effective embodiment of this invention, six numeric parameters P1, . . . , P6 are used. Every parameter ranges between 0 and 1.

The first parameter P1 is the absolute value of the linear correlation coefficient among the expressions of pairs of genes of the same combination if the correlation is positive, otherwise it is null. The second parameter P2 is analogous to P1, but is null if the linear correlation is positive. The third parameter P3 indicates the value of the quadratic correlation of the combination. The more the value of the correlation is close to 1, the more the genes of the combination are correlated.

The fourth parameter P4 indicates the percentage of genes of the group whose value of final gene expression (that is the last attribute of the gene) is greater or smaller than the initial value of gene expression (first attribute). In practice, the percentage of genes that have the same global variation is calculated.

The fifth parameter P5 indicates the percentage of genes of the group that has the same time evolution (increasing or decreasing). Finally, the last parameter P6 indicates the percentage of genes that have peak expression at the same time.

These parameters are used to verify whether the cluster contains differently expressed genes that participate in the same cellular process and so whether the relationships among them may be modeled by a Gene Network.

Using the above specified six parameters in order to determine groups of co-expressed and co-regulated genes provides a robust method of identification, capable of multi-objective discrimination.

It must be remembered that although the approach is modeled with the six parameters described above, it may be generalized to any parameter of interest that expresses a correlation of any kind. Moreover, it is possible to use parameters that may have a completely semantic biological meaning or more complex mixed parameters that express at the same time a numerical and a semantic correlation. In the latter case, public databases exist to which a query may be submitted for obtaining a numerical codification that expresses the eventual semantic correlation.

A detailed examination of the six proposed parameters is examined hereinafter.

Parameters relating to correlation (P1, P2, P3): The correlation indicates the level of relationship among genes. Through these parameters, it is possible to determine how a linear equation or any other equation is appropriate to describe or explain such a relationship.

Given that X and Y are two time profiles of gene expression, it is possible to make a scatter diagram in a system of Cartesian coordinates. Should all the points of the scatter diagram lay around a straight line, the correlation is linear. In this case the equation that ties the two variables is a linear equation:

$$Y = a + bX \tag{1}$$

If Y increases when X increases, the correlation is said to be positive or direct. If Y decreases when X increases, the correlation is said to be negative or inverse. If there is not any linear relation between the two sequences, they are said to be uncorrelated. The degree of linear correlation between two gene sequences is given by the linear correlation coefficient defined as follows:

$$\rho = \frac{\sum (X - \overline{X})(Y - \overline{Y})}{\sqrt{\sum (X - \overline{X})^2 \sum (Y - \overline{Y})^2}} \quad -1 \le \rho \le 1 \tag{2}$$

wherein the sum goes from 1 to m (being m the number of levels of expression calculated for each gene) and $$\overline{X} = \frac{\sum X}{m} \text{ and } \overline{Y} = \frac{\sum Y}{m}$$

are the mean values.

The linear correlation is maximum when the absolute value of the coefficient ρ is equal to 1 (the sign depends on the fact that a variable increases or decreases when the other variable increases).

Figure 5:
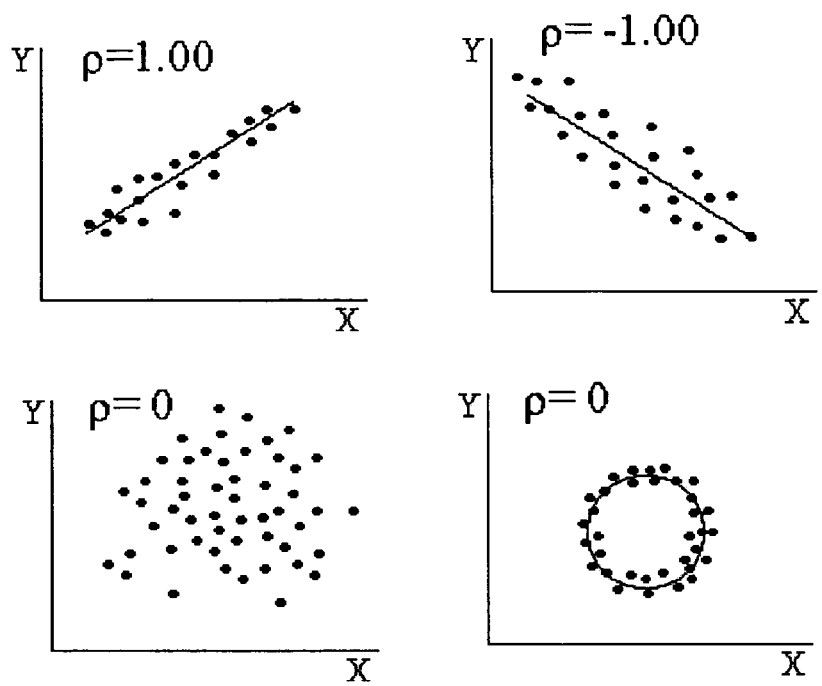
FIG. 5 shows sample scatter diagrams.

FIG. 5 illustrates examples of scatter diagrams. A null value of the linear correlation coefficient implies only the absence of a linear correlation, nevertheless two sequences may be strongly dependent from each other while not presenting a strong linear correlation. A typical case is that of points distributed along the circumference of a circle.

Figure 6:
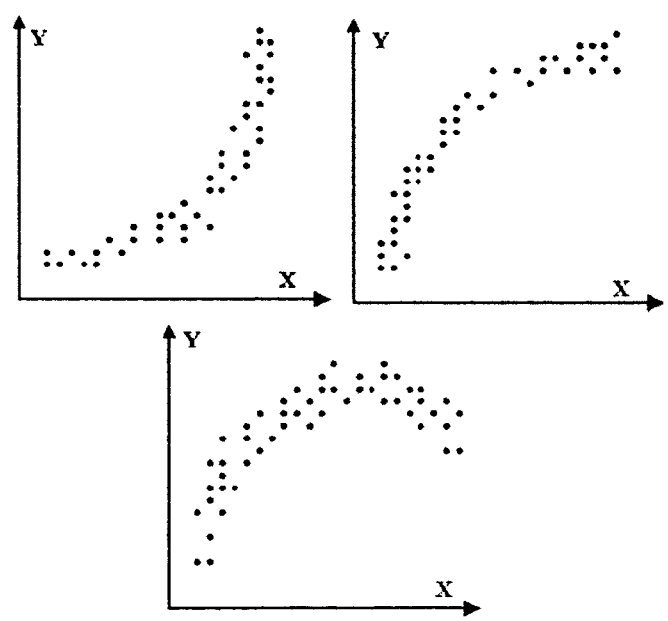
FIG. 6 shows examples of diagrams of data correlated according to a quadratic law.

Sometimes, the correlation between two gene sequences may be of a quadratic type, that is the relationship between X and Y is the equation of a parabola:

$$Y = a + bX + cX^2 \tag{3}$$

wherein a is a constant, b is the linear growth coefficient and c is tied to the curvature and is due to the relation between Y and the square power of X. FIG. 6 shows examples of quadratic correlation.

In general, whichever the relation between X and Y is, the correlation coefficient is defined as:

$$r = \pm \sqrt{\frac{\sum (Ystim - \overline{Y})^2}{\sum (Y - \overline{Y})^2}} \tag{4}$$

wherein Ystim is the interpolated value of Y obtained by the method of minimum squares. It is worth noticing that r is a non dimensional quantity, that is it does not depend on the unity of measure. When the relation between X and Y is linear, r coincides with the linear correlation coefficient, otherwise it has a more general meaning. Moreover, in the case in which the relation is linear, $$r_{XY} = r_{YX}$$

that is the quantity r is the same irrespectively from the fact that X or Y is the independent variable. In general:

$$r_{XY} \ne r_{YX}$$

As said before, the first three extracted parameters relate to the linear and to the quadratic correlation. Let us consider one of the generated combinations and let us assume that the corresponding group be constituted by n genes. When a number of gene sequences greater than two is considered, instead of the linear correlation coefficient, a linear correlation matrix R, defined as follows, is considered:

$$R = \begin{vmatrix} 1 & \rho_{12} & \cdots & \rho_{1n} \\ \rho_{21} & 1 & \cdots & \rho_{2n} \\ \cdot & \cdot & \cdots & \cdot \\ \rho_{n1} & \rho_{n2} & \cdots & 1 \end{vmatrix} \tag{5}$$

$\rho_{ij}$ being the correlation coefficient between the sequences of the gene i with the gene j. Of course, the correlation coefficient of a gene sequence with itself is 1, that is $\rho_{ij}=1$ for each i=1, ..., n.

If for each i≠j is $\rho_{ij}=0$, the n gene sequences are uncorrelated. In this case the determinant of the matrix R is 1, while in general it ranges between 0 and 1. Considering that $\rho_{ij}=1$ and that $\rho_{ij}=\rho_{ji}$, the number of calculated coefficients is:

$$\binom{n}{2} = \frac{n!}{(n-2)! * 2!} = \frac{n * (n-1)}{2} \tag{6}$$

Once these values are calculated, the interval from 0 to 1 is divided in sub-intervals, for example in five equal sub-intervals of amplitude 0.2 and the number of coefficients comprised in each sub-interval is counted. Moreover, to each sub-interval a correlation value is associated, for example equal to 0.1, 0.3, 0.5, 0.7, 0.9, respectively. If one of the five sub-intervals contains a number of coefficients greater than 50% of the total number of coefficients, the value of the first parameter is the correlation value corresponding to that interval. On the contrary, in the case in which the coefficients are distributed mainly into two intervals, the value of the first parameter is the arithmetical mean of the correlation values of these two intervals.

By assuming for example that $n_1$ coefficients are in the sub-interval to which is associated a correlation value $v_1$, $n_2$ coefficients are in the sub-interval with correlation value $v_2$, and $(n_1+n_2)>50\%$ of the total number of coefficients distributed in the five intervals, the value assigned to the first parameter P1 will be given by:

$$P1 = \frac{(v_1 * n_1 + v_2 * n_2)}{(n_1 + n_2)} \quad (7)$$

Finally, in the case in which the majority of coefficients is distributed in more than two intervals, the first parameter P1 is the mean value of all the coefficients. The first parameter is calculated considering only the coefficients $\rho_{ij}>0$.

The second parameter P2, relating to the negative linear correlation, is similarly calculated but considering the coefficients $\rho_{ij}<0$ and dividing the interval from −1 to 0 in five equal intervals.

Referring to the calculation of the third parameter P3, the correlation coefficients are calculated by considering the most general form of the correlation coefficient given in eq. (4). Considering that $r_{XY} \neq r_{YX}$, the number of coefficients to be calculated, in the case of a combination with n gene sequences, is:

$$n*(n-1) \quad (8)$$

For calculating r it is necessary to know Ystim, that is the interpolated value of Y by means of the method of minimum squares. The minimum squares parabola interpolating the set of points $(X_i, Y_i)$, with $i=1, \ldots, n$ is given by eq. (3):

$$Y=a+bX+cX^2 \quad (3)$$

wherein a, b and c are determined by solving the following three equations:

$$\begin{cases} \sum Y = aN + b\sum X + c\sum X^2 \\ \sum XY = a\sum X + b\sum X^2 + c\sum X^3 \\ \sum X^2 Y = a\sum X^2 + b\sum X^3 + c\sum X^4 \end{cases} \quad (9)$$

known as the canonical equations of the minimum squares parabola.

Given that the values of the constants are known, by substituting them in eq. (3), the value of Ystim and thus the value of r are calculated.

To the third parameter is attributed the mean value of the so calculated $n*(n-1)$ correlation coefficients.

It should be expected that the combinations CLUSTER-CLUSTER have relatively high correlation values, because the clustering criteria select groups of genes with a high level of correlation among them. Of course, even CLUSTER-FILTER and FILTER-FILTER correlations may have high correlation values. In general the correlation parameter provides more complete indications than indications obtained by using clustering criteria.

For a better understanding of this aspect, suppose for example of considering two gene sequences X and Y constituted by three values of time expression, X=[1; 5; 7] and Y=[10; 50; 70]. The relation that ties X and Y is Y=10X and so the linear correlation coefficient is 1.

Nevertheless, the clustering criteria do not highlight this kind of relationship. In fact the majority of implemented clustering techniques uses distance metrics. Two gene sequences with very similar values of gene expression are grouped in the same CLUSTER because they identify very close points in the m-dimensional space.

By contrast, in the cited example, even if there is a linear relation between two sequences, they identify distant points of the space and thus, probably, do not belong to the same CLUSTER. The only clustering criterion that make an exception to this rule is the agglomerative method using Pearson's coefficient. In fact, this metric is a measure of similarity and not of distance and does not satisfy metric properties.

Parameters relating to the pattern of expression: The last three extracted parameters, P4, P5 and P6, relate to similarity among gene sequences in terms of time-variable or condition-variable pattern of expression. In particular, the sign of the full variation is considered, the type of evolution (increasing or decreasing) and the coincidence of peak variation at the same point of time.

The fourth parameter P4 indicates the percentage of genes that behave in a similar way from the point of view of the whole variation of the value of gene expression.

For each gene sequence of the examined combination, the variation between the value of final gene expression (that is relating to the last attribute) and the initial one (relating to the first attribute) is calculated, by considering preferably only the absolute value of the variation (independently from the sign). Being the number of gene sequences that have a value of final gene expression greater that the starting known one, the percentage of sequences that have a positive variation is calculated. The fourth parameter is a number comprised between zero and one, indicative of this percentage.

In practice, the closer to 50% the percentage of genes having the same variation is, the closer to 0 the fourth parameter P4 is. The closer to 100% that percentage is, the closer to 1 the parameter P4 is, because the majority of genes of the group behaves in the same way.

In the case in which the percentage is small and close to 0, the value of the parameter is high and is close to 1. This is due to the fact that small percentages of genes having a positive variation, imply high percentages of sequences with negative variation. This parameter is used for identifying groups of genes with a similar behavior from the point of view of the whole variation of the value of gene expression, independently from the sign of the variation. Finally, percentages of 70% or equivalently of 30% are associated to values of the parameter close to 0.5.

Nevertheless, it must be considered that a gene sequence with a value of final gene expression greater than the initial value does not necessarily increase with time. Vice versa, a negative variation does not necessarily imply that the expression is decreasing. In order to identify a Gene Network, it is important to identify genes presenting a similar time evolution, whether increasing or decreasing, independently from the values of single attributes. To illustrate this let us consider FIG. 7.

The three sample gene sequences A, B, C increase with time, even if their evolution are completely different and the values of gene expression differ among them. Moreover the sequence A, even if it is increasing, has a negative variation between the final and the initial values. This detail is not considered by clustering criteria and it is not highlighted by the four parameters described above.

For this reason a fifth parameter P5 has been introduced for accounting for considering this characteristic. The percentage of genes that present an increasing evolution is calculated for each combination. In function of the obtained percentage, a value ranging from 0 to 1 is assigned to this fifth parameter.

The value assignment is very similar to that illustrated for the fourth parameter: at a very small or very large percentage value corresponds a value of the parameter close to 1, while a value of the parameter close to 0 is associated to a percentage close to 50%.

The sixth parameter P6 refers to gene sequences of the considered group that show a peak variation of the same point of time.

An external cause, such as the administering of a test drug or the changing the environmental conditions, such as sharp change in temperature, may cause a strong increase or reduction of the level of gene expression. The coincidence presence of peak variation at the same instant, may lead to the identification of a group of genes that react similarly in presence of a certain external agent.

In consideration of the fact that the values of gene expression are normalized and thus they range between 0 and 1, a threshold value of half the amplitude (0.5) of the normalization interval is considered.

The excursion peak value is calculated for each sequence belonging to the combination to be examined. If no gene of the combination has a peak variation that surpasses the threshold, a null value is assigned to the last parameter P6. If all the genes of the group have a "peak" (that is a maximum variation greater that the threshold) occurring at the same point of time, the parameter is 1. In all other cases the parameter has a value equal to the percentage of genes that show a peak at the same point of time.

Intelligent sub-system: The intelligent sub-system is based on Soft Computing methods, preferably it is a neural fuzzy system whose rules may be either:
1. introduced by the user by way of a programming language using clauses such as IF . . . THEN; or
2. generated by means of a neural network with weights and thresholds representing the characteristic parameters.

Figures 7, 8:
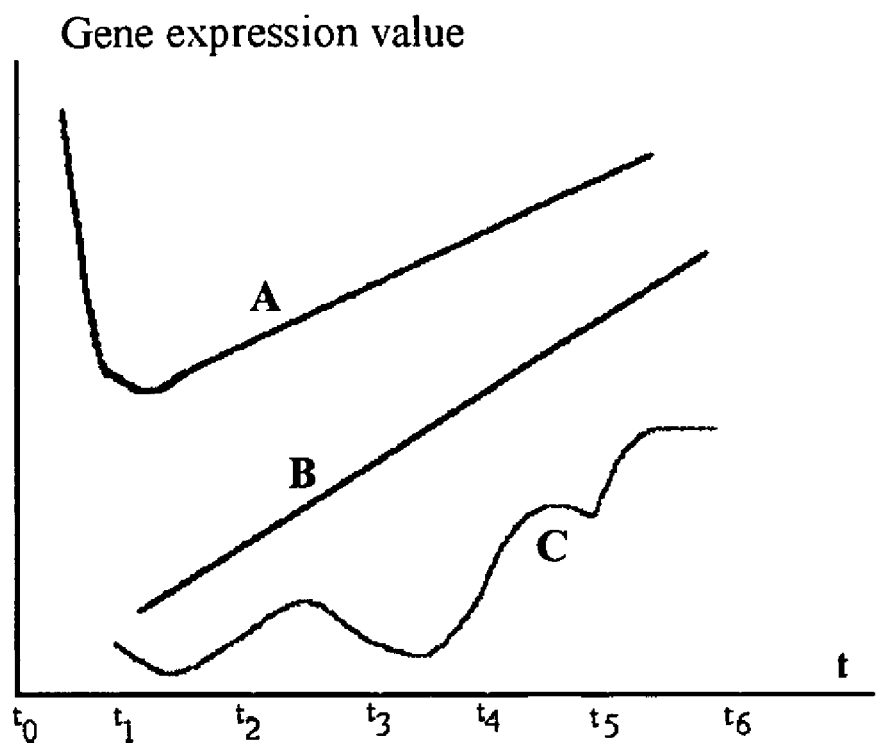
FIG. 7 shows possible time evolutions of gene sequences.
FIG. 8 shows a set of data for training the Fuzzy system of the invention.

According to the latter alternative, the sub-system must be trained first (off-line learning) with an appropriate set of data (learning matrix), such as the sample set of data of FIG. 8.

While functioning off-line, the output of the Fuzzy system (characteristic value) is compared with a threshold value THRESHOLD. Among the obtained group of genes, the groups associated to a characteristic value greater than the threshold are identified as Gene Network, while the other groups are discarded.

EXAMPLE 1

For better illustrating the method of this invention, a sample application will now be described. The input data are constituted by levels of gene expression of certain sequences to be examined. Table 2 depicts a portion of the set of data used for the experiment.

TABLE 2

| Genbank | alpha 0 | alpha 7 | alpha 14 | ... | Alpha 21 | alpha 28 | alpha 35 |
|---------|---------|---------|----------|-----|----------|----------|----------|
| YBR166C | 0.33    | −0.17   | 0.04     | ... | −0.07    | −0.09    | −0.12    |
| YOR357C | −0.64   | −0.38   | −0.32    | ... | −0.29    | −0.22    | −0.01    |
| YLR292C | −0.23   | 0.19    | −0.36    | ... | 0.14     | −0.4     | 0.16     |
| YDL120W | 0.11    | 0.32    | 0.03     | ... | 0.32     | 0.03     | −0.12    |
| YGL248W | −0.25   | 0.26    | 0.01     | ... | −0.06    | −0.42    | −0.07    |
| YIL146C | −0.58   | −0.29   | −0.45    | ... | −0.15    | −0.86    | −0.36    |
| YJR106W | −0.36   | −0.17   | −0.22    | ... | −0.34    | −0.36    | 0.03     |
| YBR123C | −0.17   | −0.32   | −0.34    | ... | −0.42    | −0.25    | −0.3     |
| ...     | ...     | ...     | ...      | ... | ...      | ...      | ...      |
| YHR047C | −0.29   | −0.07   | −0.34    | ... | −0.34    | −0.36    | −0.43    |
| YMR055C | −0.34   | 0.88    | −0.42    | ... | −0.97    | −0.15    | −0.29    |
| YDR457W | 0.01    | −0.69   | −0.09    | ... | −0.09    | 0.25     | 0.21     |

In the first column of Table 2 there are the accession numbers of genes, which in this specific case belong to the genome of the yeast *S. cerevisiae*. The first letter of each accession number is Y which stands for "yeast." Further, the name of the experiment is ALPHA and is based on 18 separate measurements at different times.

First the yeast were synchronized by withdrawal of the alpha factor. Then gene expression was measured at various time intervals. All the measurements were done by taking the value of gene expression at the instant t=0 as reference (second column of the table). The other columns show the levels of gene expression measured after 7 min, 14 min and so forth.

For each gene, identified by the corresponding accession number, it is possible to gather additional information, such as its description (Description), the functional category (Molecular Function) and the annotation (Biological Process) of the specific gene. This information is available in the Saccharomyces Genome Database, an example of which is shown in Table 3.

TABLE 3

| GenBank | Description | Molecular Function | Biological Process |
|---------|-------------|---------------------|---------------------|
| YBR166C | TYR1 TYROSINE BIOSYNTHESIS ... | GO: 8977 prephenate ... | GO: 6570 tyrosine metabolism |
| YOR357C | GRD19 SECRETION GOLGI ... |  | GO: 8104 protein localization |
| YLR292C | SEC72 SECRETION ER PROTEIN ... | GO: 5047 signal recognition ... | GO: 6615 SRP-dependent ... |
| YDL120W | YFH1 IRON HOMEOSTASIS ... | GO: 5554 unknown | GO: 6879 iron homeostasis |
| YGL248W | PDE1 PURINE METABOLISM 3', 5' ... | GO: 4115 cAMP-specific ... | GO: 19933 cAMP-mediated ... |
| YIL146C | ECM37 CELL WALL BIOGENESIS ... | GO: 5554 unknown | GO: 7047 cell wall organization ... |
| YJR106W | ECM27 CELL WALL BIOGENESIS ... | GO: 5554 unknown | GO: 7047 cell wall organization ... |
| YBR123C | TFC1 TRANSCRIPTION ... | GO: 3709 RNA polymerase III ... | GO: 6384 transcription initiation ... |
| ... | ... | ... | ... |

Results obtained with a clustering criterion: 1533 yeast genes have been considered. Each gene is described by eighteen levels of gene expression, corresponding to the values measured at intervals of 7 minutes, following the ALPHA experiment (instant t=0).

These sequences have been grouped by the K-means algorithm by adopting an initial number of centroids equal to 50 and a random method of generating centroids.

At the end of the clustering process, 50 sub-tables (CLUSTERS) were obtained, equal to the number of centroids that had been initially chosen. This condition indicates that there were no empty clusters, that eventually would have been discarded at the end of the clustering process.

TABLE 4

Cluster N. 50

| Genebank | PARAMETERS | | | | | | | | | | | |
|---|---|---|---|---|---|---|---|---|---|---|---|---|
| YPL111W | 0.16 | 0.1 | 0.86 | 1.01 | 0.99 | 1.23 | 1.9 | 1.41 | 1.51 | 0.88 | 1.04 | 1.06 | 1.04 |
| YBL005W | 1.21 | 0.82 | 1.23 | 1.34 | 1.14 | 1.14 | 1 | 0.3 | 1.24 | 1.23 | 0.72 | 1.06 | 0.64 |
| YJR028W | 1.34 | 1.28 | 1.29 | 0.77 | 1.59 | 1.1 | 1 | 1.46 | 1.22 | 1.2 | 1.79 | 1 | 0.63 |
| YGR112W | 1.23 | 1.02 | 1.01 | 1.19 | 1.04 | 1.21 | 0.7 | 1.32 | 0.82 | 0.57 | 1.43 | 0.93 | 0.53 |
| YMR058W | 0.82 | −0.15 | 0.04 | 0.16 | 0.74 | 0.82 | 1.5 | 1.17 | 1.69 | 1.65 | 1.96 | 1.7 | 1.56 |
| YOL058W | 0.55 | 1.66 | 1.94 | 1.58 | 1.3 | 0.9 | 1.1 | 0.65 | 0.7 | 0.55 | 0.93 | 0.62 | 0.9 |
| YMR011W | 1.1 | 1.84 | 2.12 | 1.65 | 1.1 | 1 | 0.7 | 0.08 | 0.36 | 0.85 | 1.99 | 1.83 | 1.55 |
| YNL036W | 0.01 | 3.1 | 2.97 | 2.83 | 2.19 | 1.9 | 1.8 | 1.04 | 1.21 | 0.83 | 0.91 | 0.42 | 0.76 |
| YHR071W | 0.77 | 1.48 | 1.96 | 2.16 | 1.61 | 1.38 | 1.3 | 1.17 | 1.18 | 0.54 | 0.88 | 0.65 | 0.96 |

| Genebank | PARAMETERS | | | | Description |
|---|---|---|---|---|---|
| YPL111W | 0.44 | 0.72 | 0.75 | 0.95 | 0.88 CAR1 ARGININE METABOLISM ARGIN |
| YBL005W | 1.09 | 0.91 | 1.12 | 0.89 | 1.22 POR3 TRANSPORT TRANSCRIPT |
| YJR028W | 1.37 | 0.88 | 0.96 | 0.38 | 0.86 NONE TRANSCRIPTION TFIIE 66 KD |
| YGR112W | 0.89 | 1 | 1.24 | 0.69 | 0.84 SHY1 RESPIRATION MITOCHONDF |
| YMR058W | 1.21 | 1.92 | 1.74 | 2.11 | 1.65 FET3 TRANSPORT CELL SURFAC |
| YOL058W | 0.87 | 1.24 | 0.8 | 1.14 | 1.07 ARG1 ARGININE BIOSYNTHESIS ARGINI |
| YMR011W | 0.7 | 0.62 | −0.29 | −0.04 | −0.09 HXT2 TRANSPORT HEXOSE PERI |
| YNL036W | 0.3 | 0.73 | 0.67 | 0.76 | 0.93 NCE103 SECRETION, NON-CLASSICAL UN |
| YHR071W | 0.78 | 0.99 | 0.97 | 0.37 | 0.67 PCL5 CELL CYCLE CYCLIN(PHO85 |

The file indicates also the accession numbers (GenBank) and the eighteen values of gene expression of the sequences (PARAMETERS) constituting the CLUSTER.

Filtering phase: According to this invention it is possible to optionally perform a filtering phase by which it is possible to select several of the considered gene sequences by function of the values of gene expression assumed at different instants. For example it is possible to filter all the sequences whose value of gene expression at the instant t=0 is greater than zero or it is possible to consider a filtering criterion relating to more than one parameter at the time. Nevertheless, this phase is optional and for sake of simplicity it has been waived for this example.

Generation of combinations: During this phase all the combinations CLUSTER-CLUSTER are generated. It is evident that, if the filtering phase had been performed, the combinations FILTER-FILTER and CLUSTER-FILTER would have been generated as well.

In this case, considering that the number of combinations is $$\binom{K}{2} = \frac{K!}{(K-2)! * 2!} = \frac{K*(K-1)}{2}$$

and considering that the number K of CLUSTERS generated in the previous phase is 50, 1225 combinations have been obtained.

For each combination the above mentioned six numerical parameters P1, . . . , P6 have been calculated. For the calculated parameters, the intelligent sub-system assigned to each combination a characteristic value ranging between 0 and 1. All the combinations with a characteristic value (degree of Gene Network), greater than a pre-established threshold have been identified as possible Gene Networks. In this example, a threshold value of 0.5 was set and six possible Gene Networks were identified. The printed file gnyeast.txt shown in Table 5 stores information relating to the generated combinations.

TABLE 5

NUMBER OF GENE-NETWORKS: 6
MAX NUMBER OF ELEMENTS: 1533

| | | | | | | DEGREE |
|---|---|---|---|---|---|---|
| gnyeast1.txt | 10 | kmyeast22.txt | kmyeast26.txt | CLUSTER 22 | CLUSTER 26 | 1 |
| gnyeast2.txt | 19 | kmyeast22.txt | kmyeast34.txt | CLUSTER 22 | CLUSTER 34 | 0.91 |
| gnyeast3.txt | 30 | kmyeast26.txt | kmyeast30.txt | CLUSTER 26 | CLUSTER 30 | 0.67 |
| gnyeast4.txt | 13 | kmyeast26.txt | kmyeast44.txt | CLUSTER 26 | CLUSTER 44 | 0.68 |
| gnyeast5.txt | 10 | kmyeast26.txt | kmyeast45.txt | CLUSTER 26 | CLUSTER 45 | 1 |
| gnyeast6.txt | 19 | kmyeast34.txt | kmyeast45.txt | CLUSTER 34 | CLUSTER 45 | 0.8 |
| Xgnyeast1.txt | 34 | kmyeast1.txt | kmyeast2.txt | CLUSTER 1 | CLUSTER 2 | 0 |
| Xgnyeast2.txt | 43 | kmyeast1.txt | kmyeast3.txt | CLUSTER 1 | CLUSTER 3 | 0.3 |
| Xgnyeast3.txt | 57 | kmyeast1.txt | kmyeast4.txt | CLUSTER 1 | CLUSTER 4 | 0 |
| Xgnyeast4.txt | 38 | kmyeast1.txt | kmyeast5.txt | CLUSTER 1 | CLUSTER 5 | 0 |
| Xgnyeast5.txt | 54 | kmyeast1.txt | kmyeast6.txt | CLUSTER 1 | CLUSTER 6 | 0 |
| Xgnyeast6.txt | 59 | kmyeast1.txt | kmyeast7.txt | CLUSTER 1 | CLUSTER 7 | 0 |
| . . . | . . . . . . | . . . | . . . | . . . | . . . | |

In the first column the names of files containing more detailed information on the generated combinations are indicated. The names of the files that start with the letter X refer to the combinations to which the intelligent sub-system assigned a value smaller than 0.5. By contrast, the remaining files refer to the combinations that the system identified as possible Gene Networks, and which in this specific case were 6.

The second column contains the number of gene sequences constituting the examined combination, while the remaining columns indicate the type of combination (example CLUSTER22-CLUSTER26).

The last column represents the value assigned from the previously trained neural fuzzy system. It is evident that the closer the assigned value is to 1, the more likely the examined combination is a Gene Network. Vice versa, the closer the output value is to 0, the more unlikely is the fact that the combination be a Gene Network.

For example looking to the third row, the combination between the CLUSTER26 (C26), containing 9 gene sequences, and the CLUSTER30 (C30), containing 21 sequences, has a value of 0.67. Thus it has been recognized as a possible gene network.

Tables 6 and 7 contain data relating to CLUSTER26 (C26) and CLUSTER30 (C30).

TABLE 6

Cluster N. 26

| Genebank | PARAMETERS | | | | | | | | | | |
|---|---|---|---|---|---|---|---|---|---|---|---|
| YDR097C | −0.56 | −0.69 | 0.7 | 1.2 | 1 | 0.4 | −0.5 | −0.67 | −0.2 | −0.54 | 1.16 | 1.24 |
| YOR074C | −1.43 | −0.6 | 0.28 | 0.79 | 0.88 | 0.28 | 0.01 | −1.03 | −0.97 | −0.4 | −0.67 | 0.45 |
| YER070W | −1.22 | −0.51 | 1.32 | 1.74 | 0.99 | 0.71 | −0.5 | −0.43 | −0.79 | −0.3 | 0.59 | 1.49 |
| YBR088C | −1.47 | −1.18 | 0.89 | 1.29 | 0.8 | −0.17 | −0.8 | 0.48 | −1.56 | −0.94 | 0.3 | 0.97 |
| YER001W | −2.18 | −0.58 | 0.87 | 1.71 | 0.64 | 0.66 | −0.3 | −0.43 | −0.97 | −0.84 | 0.18 | 1.46 |
| YOL007C | −1.43 | −1.25 | 0.83 | 0.73 | 0.77 | −0.47 | −0.3 | −1.18 | −1.47 | −0.71 | −0.32 | 0.58 |
| YPL256C | −1.69 | −0.97 | 1.11 | 1.69 | 0.45 | −0.07 | −0.6 | −1.6 | −1.79 | −1.36 | 0.07 | 1.29 |
| YIL140W | −1.43 | −1.03 | 1.37 | 0.74 | 0.26 | −0.17 | −0.8 | −1.18 | −1.09 | −1.03 | −0.45 | 0.7 |
| YMR199W | −1.6 | −0.97 | 1.25 | 0.83 | 0.9 | 0.44 | 0.03 | −0.58 | −1.15 | −0.81 | 0.62 | 1.1 |

| Genebank | PARAMETERS | | | | | | Description |
|---|---|---|---|---|---|---|---|
| YDR097C | 0.81 | 0.34 | 0.11 | 0.19 | −0.6 | −0.49 | MSH6 DNA REPAIR M |
| YOR074C | 0.44 | −0.2 | −0.56 | −0.51 | −0.92 | −1.09 | CDC21 DNA REPLICATION |
| YER070W | 0.97 | 0.44 | 0.24 | 0.36 | −0.29 | −0.47 | RNR1 DNA REPLICATION |
| YBR088C | 0.76 | −0.06 | −0.29 | −0.84 | −1.12 | −1.22 | POL30 DNA REPLICATION |
| YER001W | 1.13 | 1.1 | 0.31 | 0.07 | −0.86 | −0.76 | MNN1 PROTEIN GLYCOSYLA |
| YOL007C | 0.78 | 0.39 | −0.27 | −0.4 | −0.84 | −1.03 | CSI2 CELL WALL BIOGENESIS |
| YPL256C | 0.82 | 0.28 | −0.1 | −0.6 | −0.67 | −1.32 | CLN2 CELL CYCLE G1/9 |
| YIL140W | 0.29 | −0.36 | −0.32 | −0.51 | −0.6 | −1.32 | SRO4 BUD SITE SELECTION, |
| YMR199W | 0.95 | 0.26 | 0.31 | −0.06 | −0.45 | −0.92 | CLN1 CELL CYCLE G1/9 |

TABLE 7

Cluster N.30

| Genebank | PARAMETERS | | | | | | | | | | |
|---|---|---|---|---|---|---|---|---|---|---|---|
| YPR120C | −0.92 | −0.32 | 0.98 | 1.03 | 0.32 | −0.03 | −0.12 | −0.34 | −0.3 | −0.27 | 0.76 | 0.67 |
| YJL115W | −0.32 | 0.49 | 0.61 | 1.43 | 0.58 | 0.3 | −0.45 | −0.42 | −0.1 | 0.06 | 0.34 | 0.58 |
| YCR065W | −1.22 | −0.23 | 0.54 | 0.66 | 0.18 | 0.07 | −0.69 | −0.47 | −0.4 | −0.6 | 0.18 | 0.77 |
| YKL045W | −1.03 | −0.22 | 0.63 | 0.61 | 0.29 | −0.09 | −0.62 | −0.86 | −1 | 0.19 | 0.65 | 0.53 |
| YNL262W | 0.84 | −0.51 | 0.49 | 0.58 | 0.87 | 0.24 | −0.18 | −0.64 | −0.4 | −0.49 | 0.03 | 0.32 |
| YLR103C | −0.64 | −0.2 | 0.9 | 0.74 | 0.48 | 0.07 | −0.3 | −0.34 | −0.5 | −0.34 | 0.4 | 0.58 |
| YNL312W | −0.69 | −0.79 | 0.48 | 0.96 | 0.78 | 0.77 | 0.04 | −0.47 | −0.8 | −0.56 | 0.06 | 0.23 |
| YJL074C | −0.74 | −1.06 | 0.46 | 1.06 | 0.89 | 0.04 | −0.15 | −0.79 | −0.8 | −0.3 | 0.12 | 0.64 |
| YJL187C | −0.94 | −0.64 | −0 | 0.51 | 0.38 | −0.12 | −0.2 | −0.25 | −0.5 | −0.74 | 0.23 | 0.59 |
| YNL102W | −0.62 | 2.13 | 0.19 | 0.99 | 0.62 | −0.17 | −0.22 | −0.2 | −0.1 | −0.64 | 0.28 | 0.73 |
| YKL113C | −1.12 | −0.45 | 0.29 | 0.79 | 0.3 | −0.04 | −0.56 | −0.79 | −0.9 | −0.71 | 0.24 | 0.55 |
| YDL164C | −0.62 | −0.54 | 0.55 | 0.93 | 0.57 | −0.06 | −0.1 | −0.84 | −0.8 | −0.4 | 0.11 | 0.73 |
| YGL038C | −0.86 | −0.22 | 0.5 | 0.57 | −0.4 | 0.06 | −0.69 | −0.43 | −0.4 | 0.2 | 0.32 | 0.63 |
| YPL057C | 0.32 | −0.29 | 0.96 | 0.84 | 0.8 | 1.08 | 0.29 | −0.45 | −0.7 | 0.19 | 0.95 | 0.76 |
| YKL067W | −0.51 | 0.21 | 0.45 | 1.03 | 0.77 | 0.93 | 0.29 | −0.12 | −0.4 | −0.3 | −0.3 | −0.03 |
| YPR135W | −0.56 | −0.76 | 0.63 | 1.12 | 0.51 | −0.12 | −0.45 | −0.79 | −0.8 | −0.84 | 0.12 | 0.57 |
| YDR309C | 0.53 | −0.62 | 0.33 | 0.38 | 0.11 | −0.74 | −1.09 | −1.06 | −0.5 | −0.3 | 1.52 | 0.59 |
| YGR152C | −0.49 | −0.58 | 0.8 | 0.84 | 0.57 | 0.34 | −0.01 | −0.42 | −0.5 | −0.38 | 0.43 | 0.55 |
| YBL035C | −0.45 | −0.64 | 1.01 | 1.14 | 0.45 | −0.4 | −0.64 | 0.15 | −1.1 | 0.44 | 0.04 | 0.28 |
| YPR175W | −0.54 | −0.69 | 1.03 | 0.57 | 0.49 | −0.12 | −0.34 | −0.62 | −0.6 | −0.45 | 0.1 | 0.52 |
| YER111C | −1.25 | −0.3 | 1.32 | 1.33 | 0.5 | 0.14 | −0.89 | −0.86 | −0.8 | 0.03 | 0.85 | 0.74 |

TABLE 7-continued

Cluster N.30

| Genebank | PARAMETERS | | | | | | Description |
|---|---|---|---|---|---|---|---|
| YPR120C | 0.37 | −0.17 | 0.16 | −0.14 | −0.15 | −0.43 | CLB5 CELL CYCLE G1 |
| YJL115W | 0.36 | −0.1 | −0.32 | −0.14 | −0.42 | −0.43 | ASF1 TRANSCRIPTION |
| YCR065W | 0.66 | 0.38 | 0.1 | 0.28 | −0.4 | −0.38 | HCM1 TRANSCRIPTION(PU |
| YKL045W | 0.24 | −0.49 | −0.32 | −0.45 | −0.64 | −1.43 | PRI2 DNA REPLICATION |
| YNL262W | 0.43 | 0.08 | 0.04 | −0.56 | −0.32 | −0.71 | POL2 DNA REPLICATION |
| YLR103C | 0.33 | −0.15 | −0.25 | −0.15 | −0.45 | −0.38 | CDC45 DNA REPLICATION |
| YNL312W | 0.53 | −0.15 | 0.06 | −0.62 | −0.22 | −0.54 | RFA2 DNA REPAIR R |
| YJL074C | 0.63 | −0.17 | −0.27 | −0.45 | −0.43 | −0.2 | SMC3 CHROMATIN STRUC |
| YJL187C | 0.58 | 0.2 | 0.29 | 0.14 | −1.94 | −0.49 | SWE1 CELL CYCLE NE |
| YNL102W | 0.71 | 0.08 | 0.2 | −0.54 | −0.69 | −0.47 | POL1 DNA REPLICATION |
| YKL113C | 0.5 | −0.27 | −0.18 | −0.25 | −0.89 | −0.56 | RAD27 DNA REPAIR S |
| YDL164C | 0.6 | −0.2 | −0.25 | −0.6 | −0.56 | −0.6 | CDC9 DNA REPLICATION |
| YGL038C | 0.31 | 0.14 | −0.1 | −0.12 | −0.45 | −0.32 | OCH1 PROTEIN GLYCOSYLA |
| YPL057C | 0.58 | 0.2 | 0.34 | −0.25 | −0.42 | −0.51 | SUR1 SPHINGOLIPID METAB |
| YKL067W | 0.37 | −0.14 | 0.16 | −0.23 | −0.25 | −0.74 | YNK1 NUCLEOTIDE METAB |
| YPR135W | 0.43 | −0.29 | −0.17 | −0.45 | −0.42 | −0.71 | CTF4 DNA REPLICATION |
| YDR309C | 0.64 | −0.3 | 0.53 | −0.17 | −0.79 | −0.42 | GIC2 BUD EMERGENCE |
| YGR152C | 0.42 | 0.21 | 0.04 | −0.3 | −0.17 | −0.71 | RSR1 BUD SITE SELECTION |
| YBL035C | 0.32 | 0.03 | −0.54 | −0.12 | −0.6 | −0.3 | POL12 DNA REPLICATION |
| YPR175W | 0.3 | −0.22 | −0.15 | −0.62 | −0.2 | −0.69 | DPB2 DNA REPLICATION |
| YER111C | 0.33 | −0.23 | −0.15 | −0.58 | −0.38 | −0.51 | SWI4 CELL CYCLE TR. |

All necessary information relative to the combined set of data is reported in Table 8.

TABLE 8

| GenBank | | alpha 0 | alpha 7 | alpha 14 | alpha 21 | alpha 28 | alpha 35 | alpha 42 | alpha 49 | alpha 56 | alpha 63 | alpha 70 | alpha 77 | alpha 84 | alpha 91 | alpha 98 | alpha 105 | alpha 112 | alpha 119 |
|---|---|---|---|---|---|---|---|---|---|---|---|---|---|---|---|---|---|---|---|
| YPR120C | C30 | −0.92 | −0.32 | 0.98 | 1.03 | 0.32 | −0.03 | −0.12 | −0.34 | −0.29 | −0.27 | 0.76 | 0.67 | 0.37 | −0.17 | 0.16 | −0.14 | −0.15 | −0.43 |
| YJL115W | C30 | −0.32 | 0.49 | 0.61 | 1.43 | 0.58 | 0.3 | −0.45 | −0.42 | −0.06 | 0.06 | 0.34 | 0.58 | 0.36 | −0.1 | −0.32 | −0.14 | −0.42 | −0.43 |
| YCR065W | C30 | −1.22 | −0.23 | 0.54 | 0.66 | 0.18 | 0.07 | −0.69 | −0.47 | −0.43 | −0.6 | 0.18 | 0.77 | 0.66 | 0.38 | 0.1 | 0.28 | −0.4 | −0.38 |
| YDR097C | C26 | −0.56 | −0.69 | 0.7 | 1.2 | 1 | 0.4 | −0.47 | −0.67 | −0.2 | −0.54 | 1.16 | 1.24 | 0.81 | 0.34 | 0.11 | 0.19 | −0.6 | −0.49 |
| YKL045W | C30 | −1.03 | −0.22 | 0.63 | 0.61 | 0.29 | −0.09 | −0.62 | −0.86 | −1.03 | 0.19 | 0.65 | 0.53 | 0.24 | −0.49 | −0.32 | −0.45 | −0.64 | −1.43 |
| YNL262W | C30 | 0.84 | −0.51 | 0.49 | 0.58 | 0.87 | 0.24 | −0.18 | −0.64 | −0.43 | −0.49 | 0.03 | 0.32 | 0.43 | 0.08 | 0.04 | −0.56 | −0.32 | −0.71 |
| YOR074C | C26 | −1.43 | −0.6 | 0.28 | 0.79 | 0.88 | 0.28 | 0.01 | −1.03 | −0.97 | −0.4 | −0.67 | 0.45 | 0.44 | −0.2 | −0.56 | −0.51 | −0.92 | −1.09 |
| YER070W | C26 | −1.22 | −0.51 | 1.32 | 1.74 | 0.99 | 0.71 | −0.45 | −0.43 | −0.79 | −0.3 | 0.59 | 1.49 | 0.97 | 0.44 | 0.24 | 0.36 | −0.29 | −0.47 |
| YLR103C | C30 | −0.64 | −0.2 | 0.9 | 0.74 | 0.48 | 0.07 | −0.3 | −0.34 | −0.47 | −0.34 | 0.4 | 0.58 | 0.33 | −0.15 | −0.25 | −0.15 | −0.45 | −0.38 |
| YNL312W | C30 | −0.69 | −0.79 | 0.48 | 0.96 | 0.78 | 0.77 | 0.04 | −0.47 | −0.79 | −0.56 | 0.06 | 0.23 | 0.53 | −0.15 | 0.06 | −0.62 | −0.22 | −0.54 |
| YJL074C | C30 | −0.74 | −1.06 | 0.46 | 1.06 | 0.89 | 0.04 | −0.15 | −0.79 | −0.76 | −0.3 | 0.12 | 0.64 | 0.63 | −0.17 | −0.27 | −0.45 | −0.43 | −0.2 |
| YJL187C | C30 | −0.94 | −0.64 | −0.04 | 0.51 | 0.38 | −0.12 | −0.2 | −0.25 | −0.45 | −0.74 | 0.23 | 0.59 | 0.58 | 0.2 | 0.29 | 0.14 | −1.94 | −0.49 |
| YBR088C | C26 | −1.47 | −1.18 | 0.39 | 1.29 | 0.8 | −0.17 | −0.76 | 0.48 | −1.56 | −0.94 | 0.3 | 0.97 | 0.76 | −0.06 | −0.29 | −0.84 | −1.12 | −1.22 |
| YNL102W | C30 | −0.62 | 2.13 | 0.19 | 0.99 | 0.62 | −0.17 | −0.22 | −0.2 | −0.09 | −0.64 | 0.28 | 0.73 | 0.71 | 0.08 | 0.2 | −0.54 | −0.69 | −0.47 |
| YKL113C | C30 | −1.12 | −0.45 | 0.29 | 0.79 | 0.3 | −0.04 | −0.56 | −0.79 | −0.86 | −0.71 | 0.24 | 0.55 | 0.5 | −0.27 | −0.18 | −0.25 | −0.89 | −0.56 |
| YDL164C | C30 | −0.62 | −0.54 | 0.55 | 0.93 | 0.57 | −0.06 | −0.1 | −0.84 | −0.84 | −0.4 | 0.11 | 0.73 | 0.6 | −0.2 | −0.25 | −0.6 | −0.56 | −0.6 |
| YGL038C | C30 | −0.86 | −0.22 | 0.5 | 0.57 | −0.36 | 0.06 | −0.69 | −0.43 | −0.42 | 0.2 | 0.32 | 0.63 | 0.31 | 0.14 | −0.1 | −0.12 | −0.45 | −0.32 |
| YPL057C | C30 | 0.32 | −0.29 | 0.96 | 0.84 | 0.8 | 1.08 | 0.29 | −0.45 | −0.74 | 0.19 | 0.95 | 0.76 | 0.58 | 0.2 | 0.34 | −0.25 | −0.42 | −0.51 |
| YKL067W | C30 | −0.51 | 0.21 | 0.45 | 1.03 | 0.77 | 0.93 | −0.12 | −0.42 | −0.3 | −0.3 | −0.03 | 0.37 | −0.14 | 0.16 | −0.23 | −0.25 | −0.74 | |
| YER001W | C26 | −2.18 | −0.58 | 0.87 | 1.71 | 0.64 | 0.66 | −0.27 | −0.43 | −0.97 | −0.84 | 0.18 | 1.46 | 1.13 | 1.1 | 0.31 | 0.07 | −0.86 | −0.76 |
| YPR135W | C30 | −0.56 | −0.76 | 0.63 | 1.12 | 0.51 | −0.12 | −0.45 | −0.79 | −0.76 | −0.84 | 0.12 | 0.57 | 0.43 | −0.29 | −0.17 | −0.45 | −0.42 | −0.71 |
| YOL007C | C26 | −1.43 | −1.25 | 0.83 | 0.73 | 0.77 | −0.47 | −0.32 | −1.18 | −1.47 | −0.71 | −0.32 | 0.58 | 0.78 | 0.39 | −0.27 | −0.4 | −0.84 | −1.03 |
| YPL256C | C26 | −1.69 | −0.97 | 1.11 | 1.69 | 0.45 | −0.07 | −0.64 | −1.6 | −1.79 | −1.36 | 0.07 | 1.29 | 0.82 | 0.28 | −0.1 | −0.6 | −0.67 | −1.32 |
| YIL140W | C26 | −1.43 | −1.03 | 1.37 | 0.74 | 0.26 | −0.17 | −0.84 | −1.18 | −1.09 | −1.03 | −0.45 | 0.7 | 0.29 | −0.36 | −0.32 | −0.51 | −0.6 | −1.32 |
| YDR309C | C30 | 0.53 | −0.62 | 0.33 | 0.38 | 0.11 | −0.74 | −1.09 | −1.06 | −0.47 | −0.3 | 1.52 | 0.59 | 0.64 | −0.3 | 0.53 | −0.17 | −0.79 | −0.42 |
| YMR199W | C26 | −1.6 | −0.97 | 1.25 | 0.83 | 0.9 | 0.44 | 0.03 | −0.58 | −1.15 | −0.81 | 0.62 | 1.1 | 0.95 | 0.26 | 0.31 | −0.06 | −0.45 | −0.92 |
| YGR152C | C30 | −0.49 | −0.58 | 0.8 | 0.84 | 0.57 | 0.34 | −0.01 | −0.42 | −0.47 | −0.38 | 0.43 | 0.55 | 0.42 | 0.21 | 0.04 | −0.3 | −0.17 | −0.71 |
| YBL035C | C30 | −0.45 | −0.64 | 1.01 | 1.14 | 0.45 | −0.4 | −0.64 | 0.15 | −1.09 | 0.44 | 0.04 | 0.28 | 0.32 | 0.03 | −0.54 | −0.12 | −0.6 | −0.3 |
| YPR175W | C30 | −0.54 | −0.69 | 1.03 | 0.57 | 0.49 | −0.12 | −0.34 | −0.62 | −0.56 | −0.45 | 0.1 | 0.52 | 0.3 | −0.22 | −0.15 | −0.62 | −0.2 | −0.69 |
| YER111C | C30 | −1.25 | −0.3 | 1.32 | 1.33 | 0.5 | 0.14 | −0.89 | −0.66 | −0.79 | 0.03 | 0.85 | 0.74 | 0.33 | −0.23 | −0.15 | −0.58 | −0.38 | −0.51 |
| P1 | P2 | P3 | P4 | P5 | P6 | OUT | | | | | | | | | | | | |
| 0.81 | 0 | 0.77 | 0.5 | 0.72 | 0.57 | 0.67 | | | | | | | | | | | | |

P1 = POSITIVE LINEAR CORRELATION COEFFICIENT
P2 = NEGATIVE LINEAR CORRELATION COEFFICIENT
P3 = QUADRATIC CORRELATION COEFFICIENT
P4 = PERCENTAGE OF GENES HAVING A FINAL VALUE LARGER THAN THE INITIAL VALUE
P5 = PERCENTAGE OF GENES HAVING THE SAME TIME EVOLUTION
P6 = PERCENTAGE OF GENES HAVING A MAXIMUM EXCURSION IN THE SAME TIME INSTANT

The second column of Table 8 indicates the CLUSTER, to which the gene sequence belongs, whose the accession number of which is written in the first column. In addition to the values of gene expression of the sequences that constitute the combination, the values of the six extracted parameters and the relative output value assigned by the system are also shown.

Setting aside the calculation of the first three parameters P1, P2 and P3 relating to the linear and quadratic correlation of the combination, for the sake of simplicity, the procedure for calculating the parameters P4, P5 and P6 is described for the combination C26-C30 of Table 8.

Calculation of P4: In order to calculate the parameter P4, which is the percentage of genes whose final value is greater than the initial value, the variation $\Delta$ between the value of gene expression corresponding to the last instant alpha119 and the value of expression corresponding to the first instant alpha0 must be considered. For the first sequence YPR120C the variation $\Delta$ is:

$$\Delta = -0.43 - (-0.92) = 0.49 \Rightarrow \Delta > 0$$

This calculation is performed for all the sequences of the combination. The result is that 21 sequences out of 30, that is 70% of the sequences have a positive variation ($\Delta>0$). This percentage, which will be indicated with the variable "PERCENT_VALUE" hereinafter, is transformed in a value comprised between 0 and 1.

The transformation procedure of this variable is:
When PERCENT_VALUE=50%, P4 is null.
When 50%<PERCENT_VALUE$\leq$70%, P4 is a value ranging from 0 to 0.5 (the greater the percent value, the greater the value of the parameter).
When 70%<PERCENT_VALUE$\leq$100%, P4 is a value ranging from 0.5 to 1 (the greater the percent value, the greater the parameter).
When 30% $\leq$PERCENT_VALUE<50%, P4 is a value ranging from 0 to 0.5 (the smaller the percent value, the greater the value of the parameter).
When 0%$\leq$PERCENT_VALUE<30%, P4 is a value ranging from 0.5 to 1 (the smaller the percent value, the greater the value of the parameter).

In practice, the closer to 50% is the percentage of genes having the same variation, the closer to 0 is the value of the fourth parameter P4. The closer to 100% is the PERCENT_VALUE, the closer to 1 is the parameter P4, because the majority of genes in the group have similar behavior.

In the case in which the percentage is small and close to 0, the value of the parameter P4 is great and is close to 1. This is due to the fact that small percentages of genes having a positive variation ($\Delta>0$) imply high percentages of sequences with negative variation ($\Delta<0$). This parameter allows identification of groups of genes with a similar behavior from the point of view of the global variation of the value of gene expression, independently from the sign of the variation. Thus, for example, genes turned or on in response to a drug can be identified. In the considered example, given that the percent value is 70%, P4 has a value equal to 0.5 (see Table 8).

Calculation of P5: In order to calculate P5, which is the percentage of genes with the same time evolution, it must be verified whether the pattern of gene expression is increasing or decreasing with time.

Given that the values of gene expression are sampled, the variations $\Delta i$ between the gene expression value corresponding to the $(i)^{th}$ instant and the value of the gene expression corresponding to the $(i-1)^{th}$ for i=1, 2, . . . , n being n the number of experiments, must be calculated. In this specific case n=18 and for each sequence n-1 (17) values are calculated.

For example, for the first sequence YPR120C the values of the variations $\Delta i$ are:

$\Delta 1 = alpha7 - alpha0 = -0.32 - (0.92) = 0.6 > 0$ $\Delta 2 = alpha14 - alpha7 = 0.98 - (-0.32) = 1.3 > 0$ $\Delta 3 = alpha21 - alpha14 = 1.03 - 0.98 = 0.05 > 0$ $\Delta 4 = alpha28 - alpha21 = 0.32 - 1.03 < 0$ $\Delta 5 = alpha35 - alpha28 = -0.03 - 0.32 < 0$ $\Delta 6 = alpha42 - alpha35 = -0.12 + 0.03 < 0$ $\Delta 7 = alpha49 - alpha42 = -0.34 + 0.12 < 0$ $\Delta 8 = alpha56 - alpha49 = -0.29 + 0.34 > 0$ $\Delta 9 = alpha63 - alpha56 = -0.27 + 0.29 > 0$ $\Delta 10 = alpha70 - alpha63 = 0.76 + 0.27 > 0$ $\Delta 11 = alpha77 - alpha70 = 0.67 - 0.76 < 0$ $\Delta 12 = alpha84 - alpha77 = 0.37 - 0.67 < 0$ $\Delta 13 = alpha91 - alpha84 = -0.17 - 0.37 < 0$ $\Delta 14 = alpha98 - alpha91 = 0.16 + 0.17 > 0$ $\Delta 15 = alpha105 - alpha98 = \mathbf{-0.14 - 0.16} < 0$ $\Delta 16 = alpha112 - alpha105 = -0.15 + 0.14 < 0$ $\Delta 17 = alpha119 - alpha112 = -0.43 + 0.15 < 0$ If the number of positive variations $\Delta i$ is greater than the number of negative variations $\Delta i$, the time evolution of the sequence is globally increasing, vice versa it is globally decreasing.

For the sequence YPR120C, the number of positive variations $\Delta i$ is 7, while the number of negative variations $\Delta i$ is 10. Given that the number of positive variations $\Delta i$ is smaller than the number of negative variations $\Delta i$, the sequence is considered having a decreasing time evolution.

The same calculation is repeated for each of the remaining 29 sequences of the combination illustrated in Table 8, showing that a certain percentage of sequences (indicated hereinafter with the variable "PERCENT") has a globally increasing time evolution. To this percent value a parameter P5, whose value ranges between 0 and 1, is associated with a procedure similar to that described for the parameter P4.

In the considered case, 5 sequences out of 30, that is 16.7% have a globally increasing time evolution, thus P5 is large. In fact 83.3% of sequences have a decreasing evolution and thus a higher percentage of sequences have similar time evolutions.

It is worth remarking that the value of parameter P5 does not depend on the fact that the global evolution of the majority of genes is increasing or decreasing, but on how many genes of the combination have the same evolution. In the considered case, the parameter (P5) is close to 1.

A possible procedure for evaluating P5 is described in detail hereinafter.

Let us define three threshold values: THRESHOLD1=0.3; THRESHOLD2=1−THRESHOLD1=0.7; THRESHOLD3=0.5. In function of the thresholds the following values are calculated:

value1=((threshold2−threshold3)/(1−threshold3))=0.4;
threshold2=((2*threshold2−1+threshold3)/(2*threshold3))=0.9;

If threshold2<=percent<=1, P5=((percent−threshold1)/(1−value1));

If 0<=percent<=threshold1, P5=(((1−percent)−value1)/(1−value1));

If 0.5<=percent<threshold2, P5=((percent−0.5)/(value2−0.5));

If threshold 1 <percent<0.5, P5=(((1−percent)−0.5)/(value2−0.5)).

A percentage of 50% corresponds to a null value of P5 because, as previously stated, in this case there is not any prevalent (increasing or decreasing) time evolution of the sequences that constitute the combination.

In the proposed example (Table 8) the value of P5 is given by:

$$P5=(((1-\text{percent})-\text{value1})/(1-\text{value1}))=(1-0.167-0.4)/0.6=0.72$$

Calculation of P6: In order to calculate P6, which is the percentage of genes with a peak occurring at the same instant, it must be verified whether the absolute value of the variation $\Delta i$ exceeds a certain threshold value. Given that the values relative to each experiment have been normalized between 0 and 1, a value of 0.5, which is one half of the normalization interval, was chosen as threshold value. Table 9 contains the gene expression values normalized between 0 and 1 of the sequences constituting the combination C26-C30.

TABLE 9

|  | alpha 0 | alpha 7 | alpha 14 | alpha 21 | alpha 28 | alpha 35 | alpha 42 | alpha 49 | alpha 56 |
|---|---|---|---|---|---|---|---|---|---|
| YPR120C | 0 | 0.308 | 0.974 | 1 | 0.636 | 0.456 | 0.4103 | 0.297 | 0.323 |
| YJL115W | 0.07 | 0.5 | 0.564 | 1 | 0.548 | 0.399 | 0 | 0.016 | 0.207 |
| YCR065W | 0 | 0.497 | 0.884 | 0.945 | 0.704 | 0.648 | 0.2663 | 0.377 | 0.397 |
| YDR097C | 0.07 | 0 | 0.72 | 0.979 | 0.876 | 0.565 | 0.114 | 0.01 | 0.254 |
| YKL045W | 0.19 | 0.582 | 0.99 | 0.981 | 0.827 | 0.644 | 0.3894 | 0.274 | 0.192 |
| YNL262W | 0.98 | 0.127 | 0.759 | 0.816 | 1 | 0.601 | 0.3354 | 0.044 | 0.177 |
| YOR074C | 0 | 0.359 | 0.74 | 0.961 | 1 | 0.74 | 0.6234 | 0.173 | 0.199 |
| YER070W | 0 | 0.24 | 0.858 | 1 | 0.747 | 0.652 | 0.2601 | 0.267 | 0.145 |
| YLR103C | 0 | 0.286 | 1 | 0.896 | 0.727 | 0.461 | 0.2208 | 0.195 | 0.11 |
| YNL312W | 0.06 | 0 | 0.726 | 1 | 0.897 | 0.891 | 0.4743 | 0.183 | 0 |
| YJL074C | 0.15 | 0 | 0.717 | 1 | 0.92 | 0.519 | 0.4292 | 0.127 | 0.142 |
| YJL187C | 0.4 | 0.514 | 0.751 | 0.968 | 0.917 | 0.719 | 0.6877 | 0.668 | 0.589 |
| YBR088C | 0.03 | 0.133 | 0.86 | 1 | 0.828 | 0.488 | 0.2807 | 0.716 | 0 |
| YNL102W | 0.02 | 1 | 0.312 | 0.596 | 0.465 | 0.184 | 0.1667 | 0.174 | 0.213 |
| YKL113C | 0 | 0.351 | 0.738 | 1 | 0.743 | 0.565 | 0.2932 | 0.173 | 0.136 |
| YDL164C | 0.12 | 0.169 | 0.785 | 1 | 0.797 | 0.441 | 0.4181 | 0 | 0 |
| YGL038C | 0 | 0.43 | 0.913 | 0.96 | 0.336 | 0.617 | 0.1141 | 0.289 | 0.295 |
| YPL057C | 0.58 | 0.247 | 0.934 | 0.868 | 0.846 | 1 | 0.5659 | 0.159 | 0 |
| YKL067W | 0.13 | 0.537 | 0.672 | 1 | 0.853 | 0.944 | 0.5819 | 0.35 | 0.181 |
| YER001W | 0 | 0.411 | 0.784 | 1 | 0.725 | 0.73 | 0.491 | 0.45 | 0.311 |
| YPR135W | 0.14 | 0.041 | 0.75 | 1 | 0.689 | 0.367 | 0.199 | 0.026 | 0.041 |
| YOL007C | 0.02 | 0.096 | 1 | 0.957 | 0.974 | 0.435 | 0.5 | 0.126 | 0 |
| YPL256C | 0.03 | 0.236 | 0.833 | 1 | 0.644 | 0.494 | 0.3305 | 0.055 | 0 |
| YIL140W | 0 | 0.143 | 1 | 0.775 | 0.604 | 0.45 | 0.2107 | 0.089 | 0.121 |
| YDR309C | 0.62 | 0.18 | 0.544 | 0.563 | 0.46 | 0.134 | 0 | 0.011 | 0.238 |
| YMR199W | 0 | 0.221 | 1 | 0.853 | 0.877 | 0.716 | 0.5719 | 0.358 | 0.158 |
| YGR152C | 0.14 | 0.084 | 0.974 | 1 | 0.826 | 0.677 | 0.4516 | 0.187 | 0.155 |
| YBL035C | 0.29 | 0.202 | 0.942 | 1 | 0.691 | 0.309 | 0.2018 | 0.556 | 0 |
| YPR175W | 0.09 | 0 | 1 | 0.733 | 0.686 | 0.331 | 0.2035 | 0.041 | 0.076 |
| YER111C | 0 | 0.368 | 0.996 | 1 | 0.678 | 0.539 | 0.1395 | 0.151 | 0.178 |

|  | alpha 63 | alpha 70 | alpha 77 | alpha 84 | alpha 91 | alpha 98 | alpha 105 | alpha 112 | alpha 119 |
|---|---|---|---|---|---|---|---|---|---|
| YPR120C | 0.3333 | 0.8615 | 0.815 | 0.662 | 0.3846 | 0.554 | 0.4 | 0.39487 | 0.2513 |
| YJL115W | 0.2713 | 0.4202 | 0.548 | 0.431 | 0.1862 | 0.069 | 0.1649 | 0.01596 | 0.0106 |
| YCR065W | 0.3116 | 0.7035 | 1 | 0.945 | 0.804 | 0.663 | 0.7538 | 0.41206 | 0.4221 |
| YDR097C | 0.0777 | 0.9585 | 1 | 0.777 | 0.5337 | 0.415 | 0.456 | 0.04663 | 0.1036 |
| YKL045W | 0.7788 | 1 | 0.942 | 0.803 | 0.4519 | 0.534 | 0.4712 | 0.37981 | 0 |
| YNL262W | 0.1392 | 0.4684 | 0.652 | 0.722 | 0.5 | 0.475 | 0.0949 | 0.24684 | 0 |
| YOR074C | 0.4459 | 0.329 | 0.814 | 0.81 | 0.5325 | 0.377 | 0.3983 | 0.22078 | 0.1472 |
| YER070W | 0.3108 | 0.6115 | 0.916 | 0.74 | 0.5608 | 0.493 | 0.5338 | 0.31419 | 0.2534 |
| YLR103C | 0.1948 | 0.6753 | 0.792 | 0.63 | 0.3182 | 0.253 | 0.3182 | 0.12338 | 0.1688 |
| YNL312W | 0.1314 | 0.4857 | 0.583 | 0.754 | 0.3657 | 0.486 | 0.0971 | 0.32571 | 0.1429 |
| YJL074C | 0.3585 | 0.5566 | 0.802 | 0.797 | 0.4198 | 0.373 | 0.2877 | 0.29717 | 0.4057 |
| YJL187C | 0.4743 | 0.8577 | 1 | 0.996 | 0.8458 | 0.881 | 0.8221 | 0 | 0.5731 |
| YBR088C | 0.2175 | 0.6526 | 0.888 | 0.814 | 0.5263 | 0.446 | 0.2526 | 0.15439 | 0.1193 |
| YNL102W | 0.0177 | 0.344 | 0.504 | 0.496 | 0.273 | 0.316 | 0.0532 | 0 | 0.078 |
| YKL113C | 0.2147 | 0.712 | 0.874 | 0.848 | 0.445 | 0.492 | 0.4555 | 0.12042 | 0.2932 |
| YDL164C | 0.2486 | 0.5367 | 0.887 | 0.814 | 0.3616 | 0.333 | 0.1356 | 0.15819 | 0.1356 |
| YGL038C | 0.7114 | 0.7919 | 1 | 0.785 | 0.6711 | 0.51 | 0.4966 | 0.27517 | 0.3624 |
| YPL057C | 0.511 | 0.9286 | 0.824 | 0.725 | 0.5165 | 0.593 | 0.2692 | 0.17582 | 0.1264 |
| YKL067W | 0.2486 | 0.2486 | 0.401 | 0.627 | 0.339 | 0.508 | 0.2881 | 0.27684 | 0 |
| YER001W | 0.3445 | 0.6067 | 0.936 | 0.851 | 0.8432 | 0.64 | 0.5784 | 0.33933 | 0.365 |
| YPR135W | 0 | 0.4898 | 0.719 | 0.648 | 0.2806 | 0.342 | 0.199 | 0.21429 | 0.0663 |
| YOL007C | 0.3304 | 0.5 | 0.891 | 0.978 | 0.8087 | 0.522 | 0.4652 | 0.27391 | 0.1913 |
| YPL256C | 0.1236 | 0.5345 | 0.885 | 0.75 | 0.5948 | 0.486 | 0.342 | 0.32184 | 0.1351 |
| YIL140W | 0.1429 | 0.35 | 0.761 | 0.614 | 0.3821 | 0.396 | 0.3286 | 0.29643 | 0.0393 |

TABLE 9-continued

| | | | | | | | | | |
|---|---|---|---|---|---|---|---|---|---|
| YDR309C | 0.3027 | 1 | 0.644 | 0.663 | 0.3027 | 0.621 | 0.3525 | 0.11494 | 0.2567 |
| YMR199W | 0.2772 | 0.7789 | 0.947 | 0.895 | 0.6526 | 0.67 | 0.5404 | 0.40351 | 0.2386 |
| YGR152C | 0.2129 | 0.7355 | 0.813 | 0.729 | 0.5935 | 0.484 | 0.2645 | 0.34839 | 0 |
| YBL035C | 0.6861 | 0.5067 | 0.614 | 0.632 | 0.5022 | 0.247 | 0.435 | 0.21973 | 0.3543 |
| YPR175W | 0.1395 | 0.4593 | 0.703 | 0.576 | 0.2733 | 0.314 | 0.0407 | 0.28488 | 0 |
| YER111C | 0.4961 | 0.814 | 0.771 | 0.612 | 0.3953 | 0.426 | 0.2597 | 0.33721 | 0.2868 |

For sequence YPR120C is:

$$|\Delta 1| = |alpha7 - alpha0| = 0.307$$

$$|\Delta 2| = |alpha14 - alpha7| = 0.666$$

...

$$|\Delta 17| = |alpha119 - alpha112| = 0.14359$$

Repeating these calculations for all the sequences, the results reported in Table 10 are obtained.

| | |Δ1| | |Δ2| | |Δ3| | |Δ4| | |Δ5| | |Δ6| | |Δ7| | |Δ8| | |Δ9| | |Δ10| | |Δ11| | |Δ12| | |Δ13| | |Δ14| | |Δ15| | |Δ16| | |Δ17| |
|---|---|---|---|---|---|---|---|---|---|---|---|---|---|---|---|---|
| YPR120C | 0.30769 | 0.66667 | 0.02564 | 0.3641 | 0.17949 | 0.04615 | 0.11282 | 0.02564 | 0.01026 | 0.52821 | 0.04615 | 0.15385 | 0.27692 | 0.16923 | 0.15385 | 0.00513 | 0.14359 |
| YJL115W | 0.43085 | 0.06383 | 0.43617 | 0.45213 | 0.14894 | 0.39894 | 0.01596 | 0.19149 | 0.06383 | 0.14894 | 0.12766 | 0.11702 | 0.24468 | 0.11702 | 0.09574 | 0.14894 | 0.00532 |
| YCR065W | 0.49749 | 0.38693 | 0.0603 | 0.24121 | 0.05528 | 0.38191 | 0.11055 | 0.0201 | 0.08543 | 0.39196 | 0.29648 | 0.05528 | 0.1407 | 0.1407 | 0.09045 | 0.34171 | 0.01005 |
| YDR097C | 0.06736 | 0.72021 | 0.25907 | 0.10363 | 0.31088 | 0.45078 | 0.10363 | 0.24352 | 0.17617 | 0.88083 | 0.04145 | 0.2228 | 0.24352 | 0.11917 | 0.04145 | 0.40933 | 0.05699 |
| YKL045W | 0.38942 | 0.40865 | 0.00962 | 0.15385 | 0.18269 | 0.25481 | 0.11538 | 0.08173 | 0.58654 | 0.22115 | 0.05769 | 0.13942 | 0.35096 | 0.08173 | 0.0625 | 0.09135 | 0.37981 |
| YNL262W | 0.85443 | 0.63291 | 0.05696 | 0.18354 | 0.39873 | 0.26582 | 0.29114 | 0.13291 | 0.03797 | 0.32911 | 0.18354 | 0.06962 | 0.22152 | 0.02532 | 0.37975 | 0.1519 | 0.24684 |
| YOR074C | 0.35931 | 0.38095 | 0.22078 | 0.03896 | 0.25974 | 0.11688 | 0.45022 | 0.02597 | 0.24675 | 0.11688 | 0.48485 | 0.00433 | 0.27706 | 0.15584 | 0.02165 | 0.17749 | 0.07359 |
| YER070W | 0.23986 | 0.61824 | 0.14189 | 0.25338 | 0.09459 | 0.39189 | 0.00676 | 0.12162 | 0.16554 | 0.30058 | 0.30405 | 0.17568 | 0.17905 | 0.06757 | 0.04054 | 0.21959 | 0.06081 |
| YLR103C | 0.28571 | 0.71429 | 0.1039 | 0.16883 | 0.26623 | 0.24026 | 0.02597 | 0.08442 | 0.09442 | 0.48052 | 0.11668 | 0.16234 | 0.31169 | 0.06494 | 0.19481 | 0.22857 | 0.04545 |
| YJL312W | 0.05714 | 0.72571 | 0.27429 | 0.10286 | 0.00571 | 0.41714 | 0.29143 | 0.18286 | 0.13143 | 0.35429 | 0.09714 | 0.17143 | 0.38857 | 0.12 | 0.38857 | 0.22857 | 0.18286 |
| YJL074C | 0.15094 | 0.71698 | 0.28302 | 0.08019 | 0.40094 | 0.08962 | 0.30189 | 0.01415 | 0.21698 | 0.19811 | 0.24528 | 0.00472 | 0.37736 | 0.04717 | 0.08491 | 0.00943 | 0.10849 |
| YJL187C | 0.11858 | 0.23715 | 0.21739 | 0.05138 | 0.19763 | 0.03162 | 0.01976 | 0.07905 | 0.11462 | 0.3834 | 0.14229 | 0.00395 | 0.1502 | 0.03557 | 0.05928 | 0.82213 | 0.57312 |
| YBR088C | 0.10175 | 0.72632 | 0.14035 | 0.17193 | 0.34035 | 0.20702 | 0.43509 | 0.71579 | 0.21754 | 0.43509 | 0.23509 | 0.07368 | 0.28772 | 0.0807 | 0.19298 | 0.09825 | 0.03509 |
| YNL102W | 0.97518 | 0.68794 | 0.28369 | 0.13121 | 0.28014 | 0.01773 | 0.00709 | 0.03901 | 0.19504 | 0.32624 | 0.15957 | 0.00709 | 0.2234 | 0.04255 | 0.26241 | 0.05319 | 0.07801 |
| YKL113C | 0.35079 | 0.38743 | 0.26178 | 0.25654 | 0.17801 | 0.27225 | 0.12042 | 0.03665 | 0.07853 | 0.49738 | 0.1623 | 0.02618 | 0.40314 | 0.04712 | 0.03665 | 0.33508 | 0.17277 |
| YOL164C | 0.0452 | 0.61582 | 0.21469 | 0.20339 | 0.35593 | 0.0226 | 0.41808 | 0 | 0.24859 | 0.28814 | 0.35028 | 0.07345 | 0.45198 | 0.02825 | 0.19774 | 0.0226 | 0.0226 |
| YGL038C | 0.42953 | 0.48322 | 0.04698 | 0.62416 | 0.28188 | 0.50336 | 0.1745 | 0.00671 | 0.41611 | 0.08054 | 0.20805 | 0.21477 | 0.11409 | 0.16107 | 0.01342 | 0.22148 | 0.08725 |
| YPL057C | 0.33516 | 0.68681 | 0.06593 | 0.02198 | 0.15385 | 0.43407 | 0.40659 | 0.15934 | 0.51099 | 0.41758 | 0.1044 | 0.0989 | 0.20879 | 0.07692 | 0.32418 | 0.09341 | 0.04945 |
| YKL067W | 0.40678 | 0.13559 | 0.32768 | 0.14689 | 0.0904 | 0.36158 | 0.23164 | 0.16949 | 0.0678 | 0 | 0.15254 | 0.22599 | 0.28814 | 0.16949 | 0.22034 | 0.0113 | 0.27684 |
| YER001W | 0.41131 | 0.37275 | 0.21594 | 0.27506 | 0.00514 | 0.23907 | 0.04113 | 0.13882 | 0.03342 | 0.26221 | 0.32905 | 0.08483 | 0.00771 | 0.20308 | 0.0617 | 0.23907 | 0.02571 |
| YPR135W | 0.10204 | 0.70918 | 0.25 | 0.31122 | 0.32143 | 0.16837 | 0.17347 | 0.01531 | 0.04082 | 0.4696 | 0.22959 | 0.07143 | 0.36735 | 0.06122 | 0.14286 | 0.01531 | 0.14796 |
| YOL007C | 0.07826 | 0.90435 | 0.04348 | 0.01739 | 0.53913 | 0.06522 | 0.37391 | 0.12609 | 0.33043 | 0.16957 | 0.3913 | 0.08696 | 0.16957 | 0.28696 | 0.05652 | 0.1913 | 0.0261 |
| YPL256C | 0.2069 | 0.5977 | 0.16667 | 0.35632 | 0.14943 | 0.16379 | 0.27586 | 0.0546 | 0.12356 | 0.41092 | 0.35057 | 0.13506 | 0.15517 | 0.1092 | 0.14366 | 0.02011 | 0.18678 |
| YIL140W | 0.14286 | 0.85714 | 0.225 | 0.17143 | 0.15357 | 0.23929 | 0.12143 | 0.03214 | 0.02143 | 0.20714 | 0.41071 | 0.14643 | 0.23214 | 0.01429 | 0.06786 | 0.03214 | 0.25714 |
| YDR309C | 0.44061 | 0.36398 | 0.01916 | 0.10345 | 0.32567 | 0.1341 | 0.01149 | 0.22605 | 0.06513 | 0.69732 | 0.35632 | 0.01916 | 0.36015 | 0.31801 | 0.2682 | 0.23755 | 0.14176 |
| YMR199W | 0.22105 | 0.77895 | 0.14737 | 0.02456 | 0.1614 | 0.14386 | 0.21404 | 0.2 | 0.1193 | 0.50175 | 0.16842 | 0.05263 | 0.24211 | 0.01754 | 0.12982 | 0.13684 | 0.16491 |
| YGR152C | 0.05806 | 0.89032 | 0.02581 | 0.17419 | 0.14839 | 0.22581 | 0.26452 | 0.03226 | 0.05806 | 0.52258 | 0.07742 | 0.08387 | 0.13548 | 0.10968 | 0.21935 | 0.08387 | 0.34839 |
| YBL035C | 0.0852 | 0.73991 | 0.0583 | 0.30942 | 0.38117 | 0.10762 | 0.35426 | 0.03488 | 0.6861 | 0.17937 | 0.10762 | 0.01794 | 0.13004 | 0.25561 | 0.18834 | 0.21525 | 0.13453 |
| YPR175W | 0.08721 | 1 | 0.26744 | 0.04651 | 0.35465 | 0.12791 | 0.16279 | 0.03488 | 0.06395 | 0.31977 | 0.24419 | 0.12791 | 0.30233 | 0.0407 | 0.27326 | 0.24419 | 0.28488 |
| YER111C | 0.36822 | 0.62791 | 0.00388 | 0.32171 | 0.13953 | 0.39922 | 0.01163 | 0.02713 | 0.31763 | 0.31783 | 0.04264 | 0.15891 | 0.21705 | 0.03101 | 0.16667 | 0.07752 | 0.05039 |

The values of |Δ| that surpass the threshold are underlined. For each sequence the maximum value of |Δ| that surpasses the threshold is the peak (maximum value) and it is highlighted with a continuous line perimeter. For example, for the first gene sequence YPR120C there are only two values greater than the threshold, |Δ2|=0.66 and |Δ10|=0.52; the peak in this case is |Δ2|.

It must be noticed that not all gene sequences necessarily show a peak. In the proposed example the sequences YJL115W, YCR065W, YOR074C, YKL113C, YKL076W, YER001W and YDR309C do not show a peak.

For calculating the sixth parameter P6, the maximum number of peaks occurring at the same instant must be considered. In this example, the maximum number of peaks is 17 and they are in the column of |Δ2|. In particular, 56.7% of sequences (17 sequences out of 30) of the combination have a coincident peak and thus in this case P6 is equal to 0.57, as shown in Table 8.

The following list of References is provided for reader review. The identified references are incorporated by reference herein.
1. Luke Alphey, DNA Sequencing:from experimental methods to bioinformatics, BIOS Scientific Publishers, 1997.
2. G. Lewin, Gene IV, 1998.
3. D. L. Kirk, Biologia Oggi, Piccinini editore, Padova.
4. Chieffi, Dolfini, Malcovati, Pierantoni, Tenchini, Biologia e Genetica, EdiSES.
5. M. L. M. Anderson, Nucleic Acid Hybridization, BIOS scientific Publishers, 1999.
6. M. Schena, DNA Microarray: A Practical Approach, Oxford University Press 1999.
7. Patrik D'Haeseller, Reconstructing Gene Networks from Large Scale Gene Expression Data, The University of New Mexico, December 2000.
8. Pierre Bladi, Soren-Brunak, Bioinformatics. The Machine Learning Approach, MIT Press 1998.
9. Primer on Molecular Genetic, DOE Human Genome Program, 1992.
10. M. B. Eisen, P. T. Spellman, Patrick O. Brown, D. Botstein, Cluster Analysis and display of genome-wide expression patterns, Vol. 95, pp. 14863-14868, December 98, Genetics.
11. P. D'Haeseleer, S. Liang, R. Somogyi, Genetic Network inference: from co-expression clustering to reverse engineering, Vol. 16 no.8 2000, pages 707-726.
12. S. Huang, Gene expression profiling, genetic networks and cellular states: an integrating concept for tumorigenesis and drug discovery, 1 Jul. 1999.
13. P. Smolen, D. A. Baxter, J. H. Byrne, Mathematical Modeling of Gene Networks, Neuron, Vol.26, 567-580, June 2000.
14. Frank Höppner, Frank Klawonn, "Fuzzy Cluster Analysis: Methods for Classification Data Analysis and Image Recognition", first edition 1999.
15. Michele Scardi, "Tecniche di Analisi dei Dati in Ecologia", Version 1.2a, April 1998.
16. Daniel Boley, Vivian Borst, "Unsupervised Clustering: A Fast Scalable Method for Large Datasets", Department of Computer Science and Engineering.
17. D. L. Boley, Principal Direction Divisive Partitioning, Data Mining and Knowledge Discovery, 1999, Department of Computer Science and Engineering.
18. Kohonen T. Self-Organization and Associative Memory, Primavera 1984.
19. Flexer A. On the Use of Self-Organizing Maps for Clustering and Visualization.
20. R. J. Hataway, J. C. Bezdek, Y. Hu, Generalized Fuzzy c-Means Clustering Strategies Using Lp Norm Distances, IEEE Transactions on fuzzy system, Vol. 8, No 5, October 2000.
21. R. Krishapuram, J. Keller, A Possibilistic Approach to Clustering, IEEE Transactions on fuzzy system, Vol. 1, No 2, May 1993.
22. Lotfi A. Zadeh, "Fuzzy logic, Neural Networks, and Soft-Computing", Comm. of the ACM, March 1994, vol 37, No.3.
23. X L. Daboni, Calcolo delle probabilità ed elementi di Statistica.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A computer program product embodied on a computer readable medium that executes a method for identifying groups of co-regulated and co-expressed genes, the method comprising:
    defining a clustering criterion of data, relating to gene expression that varies with time and/or with the changing of environmental conditions, which is stored in a table;
    in function of said clustering criterion, identifying in sub-tables groups of genes that satisfy said clustering criterion;
    defining a number of logic filtering criteria of the data of said table;
    for each logic filtering criterion, generating a corresponding filtered sub-table containing data of genes having expression values which satisfy said logic filtering criterion;
    establishing pair combinations of said sub-tables by clustering and filtering the data of said table with said filtering criteria and by said clustering;
    calculating characteristic parameters of the data associated to the groups of genes of each pair combination;
    generating for each pair combination a characteristic value in function of the characteristic parameters of the groups of genes by a decision algorithm based on soft computing techniques;
    identifying the groups of genes associated with pair combinations whose characteristic value is greater than a certain pre-established threshold as being members of a network of genes involved in a particular cellular process and discarding pair combinations of groups of genes whose characteristic value is smaller than said threshold; and
    outputting to a user the group of genes within the pair combinations having characteristic values greater than the threshold in a selected data format.

2. The computer program product of claim 1, wherein said decision algorithm is a fuzzy logic algorithm having antecedents and consequents which are defined in function of said parameters.

3. The computer program product of claim 1, wherein said parameters are chosen from the group consisting of parameters tied to gene expression levels, parameters having a semantic biological meaning, and mixed parameters expressing at the same time a numerical relationship and a semantic meaning.

4. The computer program product of claim 3,
wherein said numeric parameters are chosen from a group consisting of:
absolute values of linear correlation coefficients among data associated to pairs of genes;
absolute values of quadratic correlation coefficients among data associated to pairs of genes;
percentage of genes of the pair combination having a final value of gene expression of which is greater than a respective value of initial gene expression;
percentage of genes of the pair combination having a final value of gene expression of which is smaller than a respective value of initial gene expression;
percentage of genes having values of gene expression which have a same increasing or decreasing time evolution; and
percentage of genes that have a maximum value of gene expression in a same condition; and
wherein said parameters having a semantic biological meaning are chosen from a group consisting of:
percentage of genes that have ontologies in common; and
percentage of genes that have functional domains in common.

5. The computer program product of claim 1, further comprising discarding combinations among sub-tables constituted by a number of genes smaller than a certain pre-established number, wherein genes that are comprised in both combined sub-tables are considered only once in connection with discarding.

6. The computer program product of claim 1, wherein said clustering criteria are based on algorithms chosen in a set comprising agglomerative hierarchic algorithms, non hierarchic Kmeans algorithms, hierarchic sequential Kmeans, non-hierarchic SOM and not exclusive Fuzzy Clustering.

7. The computer program product of claim 4, comprising:
calculating correlation coefficients of all pairs of gene sequences of the pair combination;
subdividing an interval from 0 to 1 in five sub-intervals of equal length and assigning to each of said sub-intervals a respective quantized value of correlation;
calculating the percentage of correlation coefficients belonging to each sub-interval;
defining for each combination an overall coefficient of linear correlation obtained as arithmetic mean of the quantized values associated to the sub-intervals containing a number of coefficient greater than 50%.

8. The method of claim 4, comprising
calculating coefficients of quadratic correlation of all pairs of gene sequences of a same combination;
defining for each combination a global coefficient of quadratic correlation obtained as an arithmetic mean of said correlation values.

9. The method of claim 4, comprising
calculating a percentage of gene sequences of the pair combination with a final value of gene expression greater than the initial value of gene expression;
defining a coefficient of global variation of the value of gene expression, comprised between 0 and 1, corresponding to said percentage.

10. The method of claim 4, comprising
calculating a percentage of gene sequences of the pair combination with an increasing time evolution;
defining a coefficient relative to the time evolution of the gene expression comprised between 0 and 1 corresponding to said percentage.

11. The method of claim 4, comprising
calculating a percentage of gene sequences of the pair combination with a value of gene expression greater than a pre-established threshold in correspondence of a same instant;
defining a coefficient of presence of maximum excursion of the level of gene expression in correspondence of the same instant, comprised between 0 and 1, corresponding to said percentage.

12. An identification computer system of groups of co-expressed and co-regulated genes, comprising:
a pre-processing sub-system input with data of a table relative to gene expressions variable with time and/or different environmental conditions, the pre-processing sub-system connected to a computer readable medium having executable instructions for generating sub-tables of data in groups of genes that satisfy a pre-established clustering criterion;
a processing sub-system of data of said sub-tables, the processing sub-system connected to a computer readable medium having executable instructions for considering all possible pairs of generated sub-tables and generating signals, for each pair of sub-tables, representing characteristic parameters of data associated to genes of that pair of sub-tables which express correlation among and between the included genes; and
an intelligent sub-system input with said signals representative of characteristic parameters, connected to a computer readable medium having executable instructions for generating for each pair of sub-tables a characteristic value determined as a function of the characteristic parameters and outputting to a user the groups of genes within each pair of sub-tables whose characteristic value is greater than a certain pre-established threshold as being members of a network of genes involved in a particular cellular process.

13. The computer system of claim 12, wherein said intelligent sub-system is a neural fuzzy logic sub-system, trained off-line.

14. A computer program product embodied on a computer readable medium that executes a method for identifying groups of co-regulated and co-expressed genes, the method comprising:
receiving a table of data relating to evolution of gene expression with time and/or with changing environmental conditions for a plurality of genes;
applying a clustering algorithm to the table of data so as to identify clusters in the form of sub-tables comprising groups of genes that satisfy certain clustering criterion;
establishing all possible pair combinations of said clusters;
for each cluster pair combination, calculating a characteristic value for the cluster pair combination as a function of a plurality of characteristic parameters determined for each cluster pair which express a level of correlation which exists among and between the genes included in that cluster pair combination;
identifying the genes associated with cluster pair combinations whose characteristic value is greater than a certain pre-established threshold as being members of a network of genes involved in a particular cellular process; and
outputting to a user the genes within the cluster pair combinations identified as being members of the network in a selected data format.

15. A computer program product embodied on a computer readable medium that executes a method for identifying groups of co-regulated and co-expressed genes, the method comprising:

receiving a table of data relating to evolution of gene expression with time and/or with changing environmental conditions for a plurality of genes;

applying a clustering algorithm to the table of data so as to identify clusters in the form of sub-tables comprising groups of genes that satisfy certain clustering criterion;

applying a filtering algorithm to the table of data so as to identify filter data in the form of sub-tables comprising groups of genes that satisfy certain filtering criteria;

establishing all possible pair combinations of said clusters, all possible pair combinations of filter data, and all possible pair combinations of clusters and filter data;

for each pair combination, calculating a characteristic value for the pair combination as a function of a plurality of characteristic parameters determined for each pair combination which express a level of correlation which exists among and between the genes included in that pair combination;

identifying the genes associated with pair combinations whose characteristic value is greater than a certain pre-established threshold as being members of a network of genes involved in a particular cellular process; and outputting to a user the genes within the pair combinations identified as being members of the network in a selected data format.

16. A computer program product embodied on a computer readable medium that executes a method for the identification of groups of co-expressed and co-regulated genes, the method comprising:

receiving data in table format relative to gene expressions which are variable with time and/or different environmental conditions;

generating sub-tables of data in groups of genes that satisfy a pre-established clustering criterion;

identifying all possible pairs of generated sub-tables;

generating signals, for each pair of sub-tables, representing characteristic parameters of data associated to genes of that pair of sub-tables which express correlation among and between the included genes;

processing said signals representative of characteristic parameters to generate for each pair of sub-tables a characteristic value determined as a function of the characteristic parameters;

identifying groups of genes from each pair of sub-tables whose characteristic value is greater than a certain pre-established threshold as being members of a network of genes involved in a particular cellular process; and outputting to a user data in a selected format including the groups of genes within each pair of sub-tables identified as being members of the network of genes.

17. An integrated circuit implementing a method for identifying groups of co-regulated and co-expressed genes implemented on an integrate circuit, the method comprising:

defining a clustering criterion of data, relating to gene expression that varies with time and/or with the changing of environmental conditions, which is stored in a table;

in function of said clustering criterion, identifying in sub-tables groups of genes that satisfy said clustering criterion;

defining a number of logic filtering criteria of the data of said table;

for each logic filtering criterion, generating a corresponding filtered sub-table containing data of genes having expression values which satisfy said logic filtering criterion;

establishing pair combinations of said sub-tables by clustering and filtering the data of said table with said filtering criteria and by said clustering;

calculating characteristic parameters of the data associated to the groups of genes of each pair combination;

generating for each pair combination a characteristic value in function of the characteristic parameters of the groups of genes by a decision algorithm based on soft computing techniques;

identifying the groups of genes associated with pair combinations whose characteristic value is greater than a certain pre-established threshold as being members of a network of genes involved in a particular cellular process and discarding pair combinations of groups of genes whose characteristic value is smaller than said threshold; and outputting to a user the group of genes within the pair combinations having characteristic values greater than the threshold in a selected data format.

18. An identification integrated circuit system of groups of co-expressed and co-regulated genes, comprising:

a pre-processing sub-system input with data of a table relative to gene expressions variable with time and/or different environmental conditions, the pre-processing sub-system implemented on an integrated circuit for generating sub-tables of data in groups of genes that satisfy a pre-established clustering criterion;

a processing sub-system of data of said sub-tables, the processing sub-system implemented on an integrated circuit for considering all possible pairs of generated sub-tables and generating signals, for each pair of sub-tables, representing characteristic parameters of data associated to genes of that pair of sub-tables which express correlation among and between the included genes; and an intelligent sub-system input with said signals representative of characteristic parameters, implemented on an integrated circuit for generating for each pair of sub-tables a characteristic value determined as a function of the characteristic parameters and outputting to a user the groups of genes within each pair of sub-tables whose characteristic value is greater than a certain pre-established threshold as being members of a network of genes involved in a particular cellular process.

19. An integrated circuit implementing a method for identifying groups of co-regulated and co-expressed genes, the method comprising:

receiving a table of data relating to evolution of gene expression with time and/or with changing environmental conditions for a plurality of genes;

applying a clustering algorithm to the table of data so as to identify clusters in the form of sub-tables comprising groups of genes that satisfy certain clustering criterion;

establishing all possible pair combinations of said clusters;

for each cluster pair combination, calculating a characteristic value for the cluster pair combination as a function of a plurality of characteristic parameters determined for each cluster pair which express a level of correlation which exists among and between the genes included in that cluster pair combination;

identifying the genes associated with cluster pair combinations whose characteristic value is greater than a certain pre-established threshold as being members of a network of genes involved in a particular cellular process; and outputting to a user the genes within the cluster pair combinations identified as being members of the network in a selected data format.

20. An integrated circuit implementing a method for identifying groups of co-regulated and co-expressed genes, the method comprising:

receiving a table of data relating to evolution of gene expression with time and/or with changing environmental conditions for a plurality of genes;

applying a clustering algorithm to the table of data so as to identify clusters in the form of sub-tables comprising groups of genes that satisfy certain clustering criterion;

applying a filtering algorithm to the table of data so as to identify filter data in the form of sub-tables comprising groups of genes that satisfy certain filtering criteria;

establishing all possible pair combinations of said clusters, all possible pair combinations of filter data, and all possible pair combinations of clusters and filter data;

for each pair combination, calculating a characteristic value for the pair combination as a function of a plurality of characteristic parameters determined for each pair combination which express a level of correlation which exists among and between the genes included in that pair combination;

identifying the genes associated with pair combinations whose characteristic value is greater than a certain pre-established threshold as being members of a network of genes involved in a particular cellular process; and outputting to a user the genes within the pair combinations identified as being members of the network in a selected data format.

21. An integrated circuit implementing a method for the identification of groups of co-expressed and co-regulated genes, the method comprising:

receiving data in table format relative to gene expressions which are variable with time and/or different environmental conditions;

generating sub-tables of data in groups of genes that satisfy a pre-established clustering criterion;

identifying all possible pairs of generated sub-tables;

generating signals, for each pair of sub-tables, representing characteristic parameters of data associated to genes of that pair of sub-tables which express correlation among and between the included genes;

processing said signals representative of characteristic parameters to generate for each pair of sub-tables a characteristic value determined as a function of the characteristic parameters;

identifying groups of genes from each pair of sub-tables whose characteristic value is greater than a certain pre-established threshold as being members of a network of genes involved in a particular cellular process; and outputting to a user data in a selected format including the groups of genes within each pair of sub-tables identified as being members of the network of genes.

* * * * *

UNITED STATES PATENT AND TRADEMARK OFFICE
CERTIFICATE OF CORRECTION

PATENT NO.       : 7,587,280 B2                                              Page 1 of 1
APPLICATION NO. : 10/723323
DATED            : September 8, 2009
INVENTOR(S)      : Alessi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 634 days.

Signed and Sealed this

Twenty-first Day of September, 2010

David J. Kappos
*Director of the United States Patent and Trademark Office*